(12) United States Patent
Mori

(10) Patent No.: US 10,663,542 B2
(45) Date of Patent: May 26, 2020

(54) MAGNETIC RESONANCE IMAGING APPARATUS WITH DIGITAL PROCESSOR INSIDE PATIENT BED

(71) Applicant: TOSHIBA MEDICAL SYSTEMS CORPORATION, Otawara-Shi, Tochigi-Ken (JP)

(72) Inventor: Akio Mori, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 779 days.

(21) Appl. No.: 14/953,176

(22) Filed: Nov. 27, 2015

(65) Prior Publication Data

US 2016/0077175 A1    Mar. 17, 2016

Related U.S. Application Data

(63) Continuation of application No. PCT/JP2014/060806, filed on Apr. 16, 2014.

(30) Foreign Application Priority Data

May 28, 2013 (JP) ................................. 2013-112340

(51) Int. Cl.
*G01R 33/36* (2006.01)
*A61B 5/055* (2006.01)
(Continued)

(52) U.S. Cl.
CPC .......... *G01R 33/3692* (2013.01); *A61B 5/055* (2013.01); *A61B 5/0555* (2013.01);
(Continued)

(58) Field of Classification Search
CPC G01R 33/3692; G01R 33/56; G01R 33/3875; G01R 33/385; G01R 33/34046;
(Continued)

(56) References Cited

U.S. PATENT DOCUMENTS 7,750,635 B2    7/2010  Van Helvoort et al.
7,834,628 B2 *  11/2010  Biber ................. G01R 33/3415
                                                       324/318
(Continued)

FOREIGN PATENT DOCUMENTS

JP    2008-312252    12/2008
JP    2009-518098     5/2009
(Continued)

OTHER PUBLICATIONS

International Search Report for PCT/JP2014/060806, dated Jul. 22, 2014, 3 pages.
(Continued)

*Primary Examiner* — Farhana A Hoque
(74) *Attorney, Agent, or Firm* — Nixon & Vanderhye P.C.

(57) ABSTRACT

According to one embodiment, an MRI apparatus includes a bed, a digital processing circuit, a first antenna, first radio communication circuitry, a second antenna, second radio communication circuitry, and an image reconstruction circuit. An object is loaded on the bed. The digital processing circuit is disposed inside the bed, acquires analogue MR signals from an RF coil which receives MR signals emitted from the object, and digitizes the acquired MR signals. The first radio communication circuitry wirelessly transmits the MR signals digitized by the digital processing circuit, by using the first antenna. The second radio communication circuitry wirelessly receives the MR signals wirelessly transmitted from the first antenna, by using the second antenna. The image reconstruction circuit reconstructs image data based on the MR signals received by the second radio communication circuitry.

7 Claims, 18 Drawing Sheets

(51) Int. Cl.
  *G01R 33/30* (2006.01)
  *G01R 33/34* (2006.01)
  *G01R 33/385* (2006.01)
  *G01R 33/3875* (2006.01)
  *G01R 33/56* (2006.01)
  *G01R 33/3415* (2006.01)

(52) U.S. Cl.
  CPC ..... G01R 33/307 (2013.01); G01R 33/34046 (2013.01); G01R 33/385 (2013.01); G01R 33/3875 (2013.01); G01R 33/56 (2013.01); *G01R 33/3415* (2013.01); *G01R 33/36* (2013.01)

(58) Field of Classification Search
  CPC .. G01R 33/307; G01R 33/36; G01R 33/3415; A61B 5/055; A61B 5/0555
  USPC .......................... 324/300–322; 600/407–435
  See application file for complete search history.

(56) References Cited

U.S. PATENT DOCUMENTS

| | | | | |
|---|---|---|---|---|
| 7,924,007 B2* | 4/2011 | Arnold | ............... | G01R 33/3415 324/309 |
| 8,055,196 B2* | 11/2011 | Biber | ................ | G01R 33/3607 455/39 |
| 8,467,846 B2* | 6/2013 | Rezzonico | ........... | A61B 5/0555 324/300 |
| 9,612,304 B2* | 4/2017 | Biber | ................ | G01R 33/3415 |
| 9,817,089 B2* | 11/2017 | Biber | ..................... | G01R 33/30 |
| 2008/0045830 A1* | 2/2008 | Rezzonico | ........... | A61B 5/0555 600/415 |
| 2008/0211502 A1* | 9/2008 | Arnold | ............... | G01R 33/3415 324/318 |
| 2008/0309341 A1 | 12/2008 | Dooms et al. | | |
| 2009/0286478 A1* | 11/2009 | Biber | ................ | G01R 33/3607 455/41.2 |
| 2009/0322335 A1 | 12/2009 | Adachi et al. | | |
| 2011/0101977 A1 | 5/2011 | Nakanishi et al. | | |
| 2013/0241547 A1* | 9/2013 | Biber | ................ | G01R 33/3415 324/307 |
| 2014/0021956 A1* | 1/2014 | Tomiha | ............... | G01R 33/3692 324/322 |
| 2014/0097844 A1* | 4/2014 | Tomiha | ............... | G01R 33/3692 324/321 |
| 2015/0168513 A1* | 6/2015 | Mori | ................... | G01R 33/3621 324/322 |
| 2016/0077175 A1* | 3/2016 | Mori | ................... | G01R 33/3692 324/321 |

FOREIGN PATENT DOCUMENTS

| | | |
|---|---|---|
| JP | 2010-29644 | 2/2010 |
| JP | 2011-92553 | 5/2011 |
| JP | 2012-85970 | 5/2012 |
| WO | WO 2014/017419 | 1/2014 |
| WO | WO 2014/042180 | 3/2014 |

OTHER PUBLICATIONS

English Translation of International Preliminary Report on Patentability dated Dec. 1, 2015 for Application No. PCT/JP2014/060806.
JP Office Action dated Oct. 18, 2016 in JP 2013-112340.

* cited by examiner 24 reception RF coil
25 connection ports
28 radio communication device
29 digital processing circuit

MAGNETIC RESONANCE IMAGING APPARATUS WITH DIGITAL PROCESSOR INSIDE PATIENT BED

CROSS-REFERENCE TO RELATED APPLICATIONS

This application is a Continuation Application of No. PCT/JP2014/60806, filed on Apr. 16, 2014, and the PCT application is based upon and claims the benefit of priority from Japanese Patent Application No. 2013-112340, filed on May 28, 2013, the entire contents of which are incorporated herein by reference.

FIELD

Embodiments described herein relate generally to magnetic resonance imaging apparatus.

BACKGROUND

MRI is an imaging method which magnetically excites nuclear spin of an object (a patient) placed in a static magnetic field with an RF pulse having the Larmor frequency and reconstructs an image based on MR signals generated due to the excitation. The above-described MRI means magnetic resonance imaging, the RF pulse means a radio frequency pulse, and the MR signal means a nuclear magnetic resonance signal.

Here, an RF (Radio Frequency) coil device is a device which transmits an RF pulse to nuclear spin inside an object by, for example, supplying a coil with an RF pulse electric current and receives generated MR signals.

Some of RF coil devices are built-in type included in an MRI apparatus and other RF coil devices are recognized by a control unit of the MRI apparatus by being connected to a connection port of the MRI apparatus such as local RF coil devices, for example.

Various types of the local RF coil devices are used in accordance with an imaging part. For example, in the case of imaging of a shoulder joint, a dedicated RF coil device for a shoulder joint is set on the shoulder of an object.

As a method of transmitting MR signals received by an RF coil device to a control side of an MRI apparatus, a wired transmission method and a radio transmission method in which MR signals are converted into digital signals and then wirelessly transmitted are known.

It is preferable that noise mixed with MR signals is as small as possible in terms of improving imaging quality regardless of methods of transmitting MR signals received by an RF coil device to a control side of an MRI apparatus.

Therefore, a new technology to suppress mixing of noise into MR signals by simple device configuration has been desired in MRI.

DETAILED DESCRIPTION

According to one embodiment, an MRI apparatus includes: a bed on which an object is loaded; a digital processing circuit configured to be disposed inside the bed, to acquire analogue nuclear magnetic resonance signals from an RF coil which receives nuclear magnetic resonance signals emitted from the object, and to digitize the analogue nuclear magnetic resonance signals; a first antenna; first radio communication circuitry configured to wirelessly transmit nuclear magnetic resonance signals digitized by the digital processing circuit, by using the first antenna; a second antenna; second radio communication circuitry configured to receive digitized nuclear magnetic resonance signals wirelessly transmitted from the first antenna, by using the second antenna; and an image reconstruction circuit configured to reconstruct image data based on the digitized nuclear magnetic resonance signals received by the second radio communication circuitry.

MRI apparatuses and MRI methods according to embodiments will be described with reference to the accompanying drawings. Note that the same reference numbers are given for identical components in each figure, and duplicate explanation is omitted.

<First Embodiment>

Figure 1:
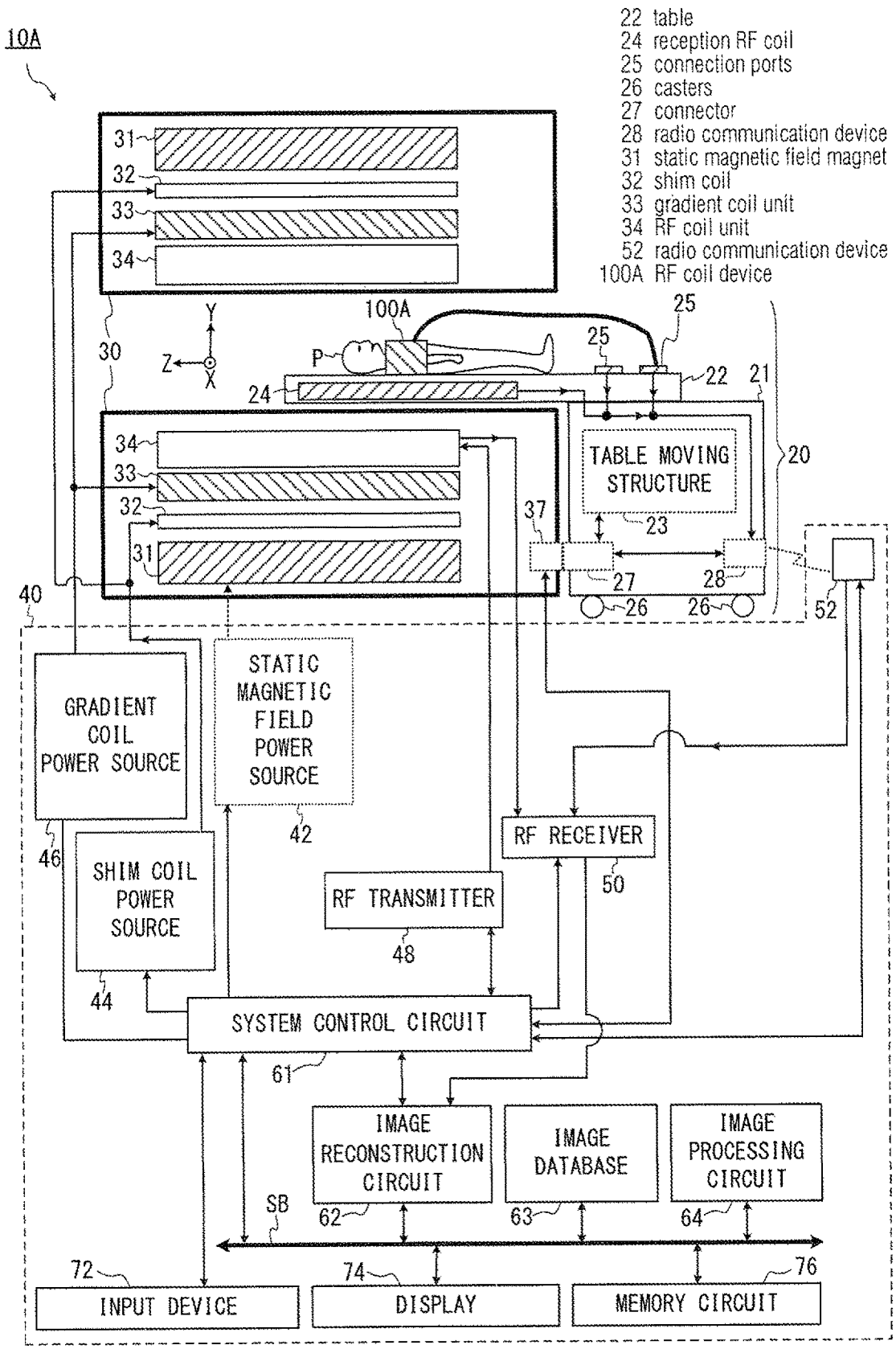
FIG. 1 is a block diagram showing an example of overall configuration of the MRI apparatus of the first embodiment.

FIG. 1 is a block diagram showing an example of overall configuration of the MRI apparatus 20A according to the first embodiment. As an example here, the components of the MRI apparatus 10A will be explained by sorting them into three groups: a bed 20, a gantry 30, and a control device 40.

Firstly, the bed 20 includes a supporting platform 21, a table 22, and a table moving structure 23 disposed inside the supporting platform 21. An object P is loaded on the top surface of the table 22. In addition, a reception RF coil 24 which receives MR signals from the object P is disposed inside the table 22. Moreover, plural connection ports 25 to which wearable type RF coil devices are connected are disposed on the top surface of the table 22.

As an example here, it is assumed that a wearable type RF coil device 100A which receives MR signals from the chest part is attached on the object P.

The supporting platform 21 supports the table 22 in such a manner that the table 22 can move in the horizontal direction (the Z axis direction in the apparatus coordinate system). In addition, since the supporting platform 21 includes casters 26 on its bottom aspect, the bed 20 is configured so as to be capable of loading a patient in another room, then moving into an imaging room, and docking with the gantry 30 in an imaging room.

Inside the supporting platform 21, the connector 27 and the radio communication device 28 are disposed.

The connector 27 is connected to the connector 37 described below of the gantry 30, when the bed 20 docks with the gantry 30.

The radio communication device 28 wirelessly transmits the MR signals received by the reception RF coil 24 and the MR signals received by RF coil devices attached on the object P such as the RF coil device 100A, to the control device 40 side in a digitized state.

The table moving structure 23 adjusts the position of the table 22 in the vertical direction by adjusting the height of the bed 21, when the table 22 is located outside the gantry 30.

In addition, the table moving structure 23 inserts the table 22 into inside of the gantry 30 by moving the table 22 in the horizontal direction and moves the table 22 to outside of the gantry 30 after completion of imaging.

Secondly, the gantry 30 is shaped in the form of a cylinder, for example, and is installed in an imaging room.

The gantry 30 includes a static magnetic field magnet 31, a shim coil 32, a gradient coil unit 33, an RF coil unit 34, and a connector 37.

The static magnetic field magnet 31 is, for example, a superconductivity coil and shaped in the form of a cylinder. The static magnetic field magnet 31 forms a static magnetic field in an imaging space by using electric currents supplied from the static magnetic field power source 42 of the control device 40 described below.

The above-described imaging space means, for example, a space in the gantry 30 in which the object P is placed and to which the static magnetic field is applied.

Note that the static magnetic field power source 42 may be omitted by configuring the static magnetic field magnet 31 as a permanent magnet.

The shim coil 32 is, for example, shaped in the form of a cylinder and arranged inside the static magnetic field magnet 31 so as to become coaxial with the static magnetic field magnet 31. The shim coil 32 forms an offset magnetic field which uniforms the static magnetic field by consuming electric currents supplied from the shim coil power source 44 of the control device 40 described below.

The gradient coil unit 33 is, for example, shaped in the form of a cylinder and arranged inside the shim coil 32. The gradient coil unit 33 includes a non-illustrated X axis gradient coil, a non-illustrated Y axis gradient coil, and a non-illustrated Z axis gradient coil.

In this specification, the X axis, the Y axis and the Z axis are assumed to be those of the apparatus coordinate system unless otherwise specifically noted. As an example here, the X axis, Y axis, and Z axis of the apparatus coordinate system are defined as follows.

First, the Y axis direction is defined as the vertical direction, and the table 22 is disposed in such a position that the direction of the normal line of its top surface becomes identical to the Y axis direction. The horizontal moving direction of the table 22 is defined as the Z axis direction, and the gantry 30 is installed in such a manner that its axis direction becomes identical to the Z axis direction. The X axis direction is the direction perpendicular to these Y axis direction and Z axis direction, and is the width direction of the table 22 in the example of FIG. 1.

The above X axis gradient coil, Y axis gradient coil, and Z axis gradient coil (not shown) form a gradient magnetic field Gx in the X axis direction, a gradient magnetic field Gy in the Y axis direction, and a gradient magnetic field Gz in the Z axis direction, respectively, in an imaging region in accordance with electric currents supplied from the gradient coil power source 46 described below.

Thereby, directions of a gradient magnetic field Gss in a slice selection direction, a gradient magnetic field Gpe in a phase encoding direction, and a gradient magnetic field Gro in a readout (frequency encoding) direction can be arbitrarily selected as logical axes, by combining the gradient magnetic fields Gx, Gy and Gz in the X axis, the Y axis and the Z axis directions as three physical axes of the apparatus coordinate system.

The above-described imaging region means, for example, at least a part of an acquisition range of MR signals used to generate one image or one set of images, which becomes an image. The imaging region is defined, for example, as a part of the imaging space by the apparatus coordinate system. For instance, when MR signals are acquired in a range wider than a region made into an image in order to prevent aliasing (artifact), the imaging region is a part of the acquisition range of MR signals. On the other hand, in some cases, the entire acquisition range of MR signals becomes an image, i.e. the imaging region and the acquisition range of MR signals agree with each other. In addition, the above one set of images means, for example, plural images when MR signals of the plural images are acquired in a lump in one pulse sequence such as multi-slice imaging.

The RF coil unit 34 is, for example, shaped in the form of a cylinder and arranged inside the gradient coil unit 33. The RF coil unit 34 includes a whole body coil which combines a function of transmitting RF pulses and a function of receiving MR signals, and a transmission RF coil that exclusively performs transmission of RF pulses, for example.

Thirdly, the control device 40 includes the static magnetic field power source 42, the shim coli power source 44, a gradient coil power source 46, an RF transmitter 48, an RF receiver 50, a radio communication device 52, a system control circuit 61, a system bus SB, an image reconstruction circuit 62, an image database 63, an image processing circuit 64, an input device 72, a display 74, and a memory circuit 76.

The gradient coil power source 46 supplies electric currents for forming the gradient magnetic field Gx, the gradient magnetic field Gy, and the gradient magnetic field Gz to each of the non-illustrated X axis gradient coil, the Y axis gradient coil, and the Z axis gradient coil of the gradient coil unit 33.

The RF transmitter 48 generates RF pulse electric currents of the Larmor frequency for causing nuclear magnetic resonance in accordance with control information inputted from the system control circuit 61, and outputs the generated RF pulse electric currents to the RF coil unit 34. The RF pulses in accordance with these RF pulse electric currents are transmitted from the RF coil unit 34 to the object P.

The whole body coil of the RF coil unit 34, the reception RF coil 24, and the RF coil device 100A receive MR signals generated due to excited nuclear spin inside the object P by the RF pulses, and the received MR signals are inputted to the RF receiver 50.

The radio communication device 52 receives electromagnetic waves of digitized MR signals wirelessly transmitted from the radio communication device 28 of the bed 20. The radio communication device 52 extracts the original digitized MR signals from the received electromagnetic waves, and outputs the extracted MR signals to the RF receiver 50. As to details of the digital radio communication, it will be explained with FIG. 6 below. Note that, as an example in the first embodiment, wireless signal transmission is performed only between the radio communication device 28 and the radio communication device 52, and signals and electric power are transmitted by wire in the rest of the MRI apparatus 10A.

The RF receiver 50 generates raw data which are digitized complex number data of MR signals obtained by performing predetermined signal processing on the MR signals inputted from the RF coil unit 34 and the radio communication device 52. The RF receiver 50 outputs the generated raw data of MR signals to the image reconstruction circuit 62.

The system control circuit 61 performs system control of the MRI apparatus 10A in setting of imaging conditions of a main scan, an imaging operation, and image display after imaging through interconnection such as the system bus SB.

The above-described term "imaging condition" refers to under what condition RF pulses or the like are transmitted in what type of pulse sequence, or under what condition MR signals are acquired from the object P, for example.

As parameters of the imaging conditions, for example, there are an imaging region as positional information in the imaging space, a flip angle, a repetition time, the number of slices, an imaging part and the type of pulse sequence such as spin echo and parallel imaging. The above imaging part means a region of the object P to be imaged, such as the head, the chest, and the abdomen.

The above-described "main scan" is a scan for imaging an intended diagnosis image such as a T1 weighted image, and it does not include a scan for acquiring MR signals for a scout image or a tuning scan (calibration scan). A scan is an operation of acquiring MR signals, and it does not include image reconstruction processing.

The above-described tuning scan is a scan for determining unconfirmed elements of imaging conditions, conditions and data used for image reconstruction processing and correction processing after the image reconstruction, and the tuning scan is performed separately from the main scan.

As an example of a tuning scan, there is a sequence of calculating the center frequency of the RF pulses used in the main scan. A prescan is a tuning scan which is performed before the main scan.

In addition, the system control circuit 61 causes the display 74 to display screen information for setting imaging conditions, sets the imaging conditions on the basis of command information from the input device 72. In addition, the system control circuit 61 causes the display 74 to display images indicated by the generated display image data after completion of imaging.

Moreover, the system control circuit 61 stores control information needed in order to cause the gradient coil power source 46, the RF transmitter 48, and the RF receiver 50 to drive. The above-described control information includes, for example, sequence information describing operation control information such as intensity, application period and application timing of the pulse electric currents which should be applied to the gradient coil power source 46.

The system control circuit 61 generates the gradient magnetic fields Gx, Gy and Gz and RF pulses by driving the gradient coil power source 46, the RF transmitter 48, and the RF receiver 50 in accordance with a predetermined sequence stored.

The input device 72 includes input tools such as a mouse and a keyboard and an input circuit which transfers contents inputted via the input tools to each component such as the system control circuit 61. Thereby, the input device 72 provides a user with a function to set imaging conditions and image processing conditions. Incidentally, it may be interpreted that the input device 72 and the display configure a GUI (Graphical User Interface).

The image reconstruction circuit 62 arranges and stores the raw data of MR signals inputted from the RF receiver 50 as k-space data, in accordance with the phase encode step number and the frequency encode step number. The above k-space means a frequency space.

The image reconstruction circuit 62 generates image data of the object P by performing image reconstruction processing including two-dimensional or three-dimensional Fourier transformation and so on. The image reconstruction circuit 62 stores the generated image data in the image database (image storage circuit) 63.

The image processing circuit 64 takes in the image data from the image database 63, performs predetermined image processing on them, and stores the image data being subjected to the image processing in the memory circuit 76 as display image data.

The memory circuit 76 stores the display image data after adding accompanying information such as the imaging conditions used for generating the display image data and information of the object P (patient information) to the display image data.

Although the components of the MRI apparatus 10A are sorted into three groups (the gantry 30, the bed 20 and the control device 40) in the above explanation, this is only an example of interpretation.

For example, the table moving structure 23 may be interpreted as a part of the control device 40.

As an example here, though it is assumed that the RF coil device 100A is a part of the MRI apparatus 10A, this is only an example of interpretation. The RF coil device 100A may be interpreted as a separate component independent of the MRI apparatus 10A. In the present embodiment, various wearable RF coil devices such as an RF coil device for the shoulder, an RF coil device for the heart, an RF coil device for the lumbar part, an RF coil device for the knee can be used for reception of MR signals in the MRI apparatus 10A, in addition to the above RF coil device 100A for the chest part. These RF coil devices may be similarly interpreted as a part of the MRI apparatus 10A or may be interpreted as separate components independent of the MRI apparatus 10A.

Figure 2:
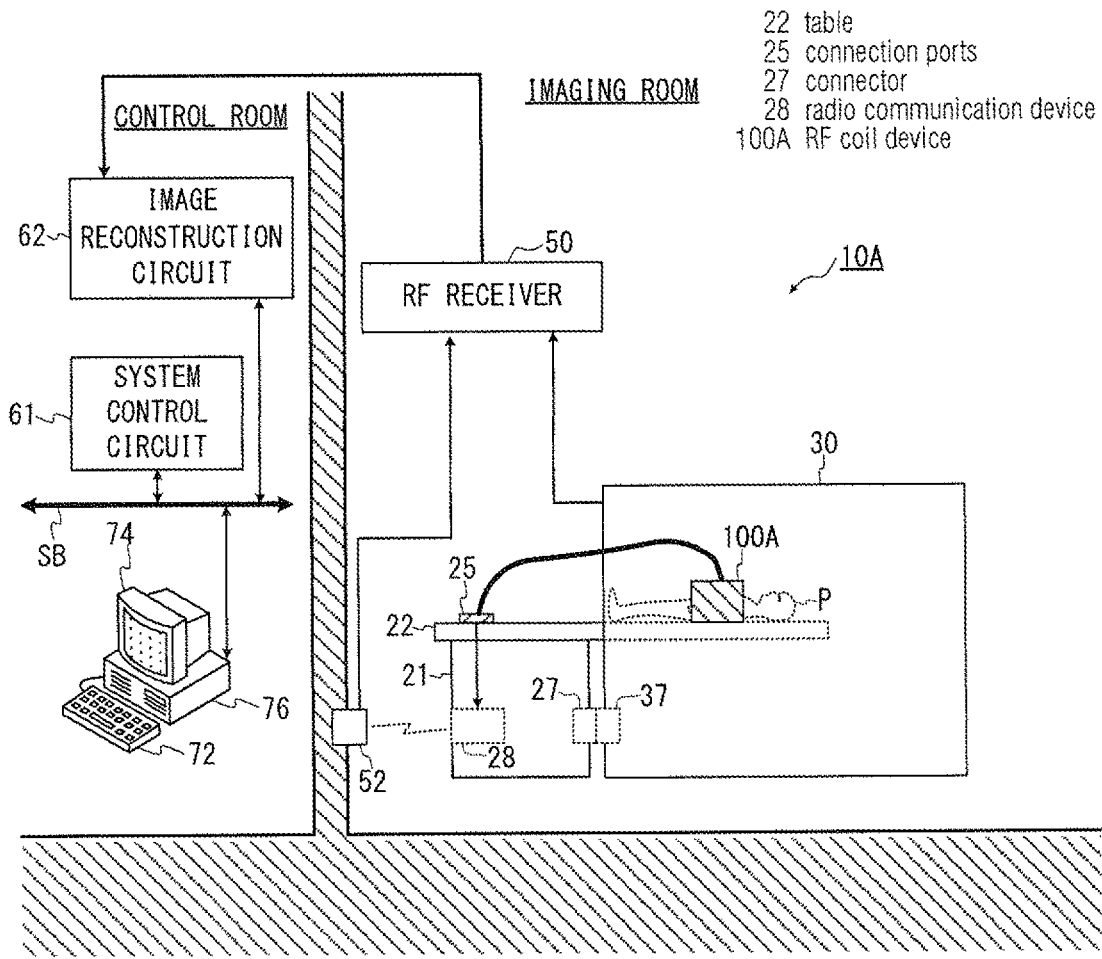
FIG. 2 is a schematic diagram showing an example of arrangement of each component of the MRI apparatus of the first embodiment, in an imaging room and a control room.

FIG. 2 is a schematic diagram showing an example of the arrangement of each component of the MRI apparatus 10A of the first embodiment, in the imaging room and the control room. The radio communication device 52 of the control device 40 is, for example, fixed to the wall of the imaging room. The radio communication device 28 of the bed 20 is disposed to a position opposite to the connector 27 in the supporting platform 21.

In other words, the radio communication device 28 is disposed on the opposite side of the gantry 30, so that anything is not interposed between the radio communication device 52 fixed to the wall of the imaging room and the radio communication device 28 of the bed 20 after being docked to the gantry 30. This is because radio communication is performed by using electromagnetic waves for remote wireless communication between the radio communication device 28 and the radio communication device 52 and communication error should be minimized between the both.

In addition, though only some of them are shown in FIG. 2 in order to avoid complication, the system control circuit 61, the system bus SB, the image reconstruction circuit 62, the image database 63, the image processing circuit 64, the input device 72, the display 74, and the memory circuit 76 are, for example, disposed in the control room (these components may be configured as one computer).

Figure 3:
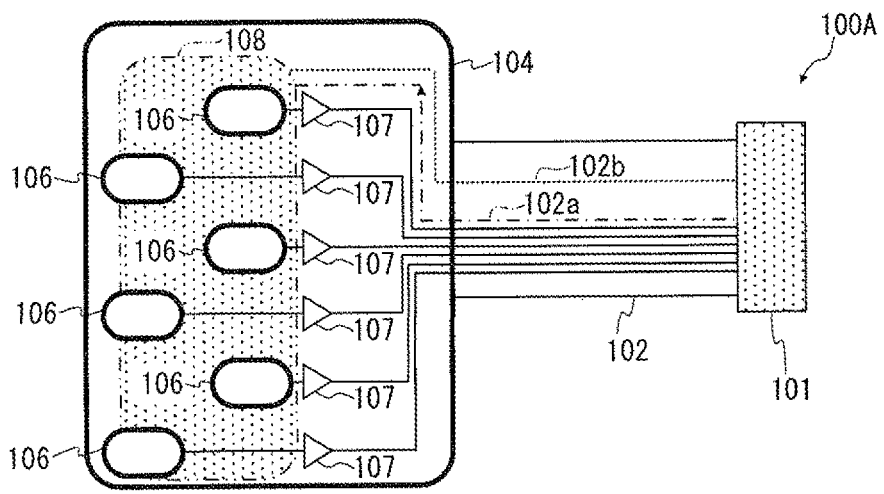
FIG. 3 is a schematic planimetric diagram showing an example of the configuration of the RF coil device shown in FIG. 1.

FIG. 3 is a schematic planimetric diagram showing an example of the configuration of the RF coil device 100A shown in FIG. 1. As shown in FIG. 3, the RF coil device 100A includes a connector 101, a cable 102, and a cover member 104.

The cover member 104 is made of a flexible material and is capable of deformation such as folding. As such a deformable (flexible) material, for example, a flexible circuit board (Flexible Printed Circuit: FPC) described in Japanese Patent Application Laid-open Publication No. 2007-229004 can be used.

Inside the cover member 104, plural coil elements, which function as antennas detecting the MR signals from the object P, are disposed. Although six coil elements 106 for the chest part are shown in FIG. 3 as an example here, the number and shape of the coil elements 106 are not limited to the shown number and shape.

In addition, inside the cover member 104, preamplifiers (radio frequency amplifier) 107 corresponding to the respective coil elements 106 are disposed. Each of the preamplifiers 107 amplifies the analogue MR signals detected by the corresponding coil element 106, and outputs the amplified MR signals to the connector 101 side. Note that, components such as a band pass filter may be further inserted between each of the preamplifiers 107 and the connector 101.

In addition, the RF coil device 100A includes a control circuit 108 inside the cover member 104. The control circuit 108 stores the identification information of the RF coil device 100A, and controls the operation of the RF coil device 100A.

Inside the cable 102, six signal lines of the MR signals corresponding to the respective preamplifiers 107 inside the cover member 104, an electric power line 102a, and a control signal line 102b are included.

The configuration of the RF coil device 100A may be the same as an RF coil device of conventional technology. Thus, each of the connection ports 25 of the table 22 in FIG. 1 can be connected (interdigitated) with the connector 101 of the RF coil device of conventional type including the RF coil device 100A.

In other words, though the number or shape of terminals of the connection part of the connection ports 25 may be the same as terminals of the MRI apparatus of conventional technology, the present embodiment is different from conventional technology in that the digital processing circuit 29 is disposed in each of the connection ports 25. The connector 101 is electrically connected to hard-wiring inside the connection ports 25 under the interdigitated state.

Figure 4:
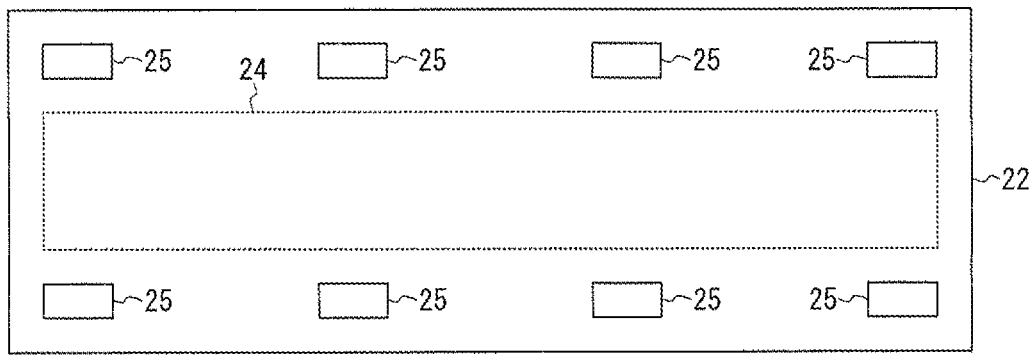
FIG. 4 is a schematic planimetric diagram showing an example of arrangement of connection ports on the table in the first embodiment.

FIG. 4 is a schematic planimetric diagram showing an example of the arrangement of the connection ports 25 on the table 22 in the first embodiment. As an example here, eight connection ports 25 are arranged on the top surface side of the table 22.

The object P is, for example, loaded in the middle of the width direction (the X axis direction in FIG. 1) of the table 22. Thus, in this example, on both end sides in the width direction of the table 22, four of the connection ports 25 are arranged along the longer direction of the table 22 (the Z axis direction) in a row at intervals.

In addition, the number or arrangement position of the connection ports 25 is not limited to that of FIG. 4. For example, several number of the connection ports 25 may be separately disposed only on the one end side and the other end side in the longer direction of the table 22.

Figure 5:
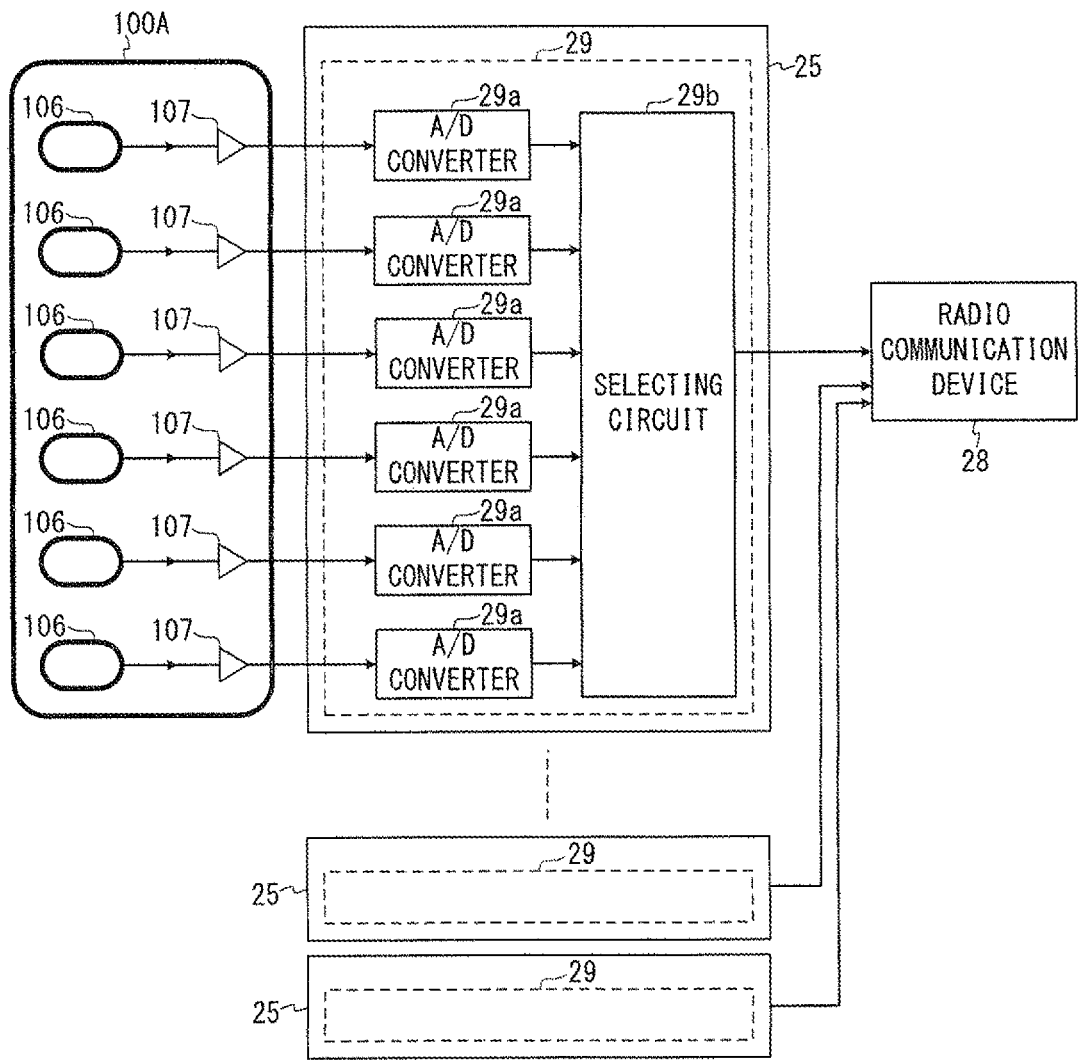
FIG. 5 is a block diagram showing an example of configuration of a digital processing circuit in each of the connection ports of the first embodiment.

Moreover, in the first embodiment, the digital processing circuit 29 that converts the analogue MR signals inputted from the RF coil device 100A into digital signals are included in each of the connection ports 25 (see the next FIG. 5).

FIG. 5 is a block diagram showing an example of the configuration of the digital processing circuit 29 in each of the connection ports 25 of the first embodiment. The digital processing circuit 29 converts the MR signals outputted from the RF coil device 100A into digital signals for each channel by using a direct sampling method, and outputs the digitized MR signals to the radio communication device 28. The digital processing circuit 29 includes plural A/D (analog to digital) converters 29a and a selecting circuit 29b.

The above-described direct sampling method is a signal processing method in which an analogue signal is directly subjected to A/D conversion without performing frequency conversion and is detected. When the direct sampling method is performed on the MR signals, detection of digital signals is performed by using carrier for detecting MR signals generated by a DDS (direct digital synthesizer).

Incidentally, the above-described direct digital synthesizer is a circuit or a system which generates an arbitrary waveform or frequency in a digital manner.

The above-described "channel" means each pathway of plural analogue MR signals outputted from the RF coil device 100A and the number of channels is, for example, equal to the number of the coil elements 106 inside the RF coil device 100A.

More specifically, in conventional technology in which the MR signals outputted from the RF coil device 100A are transmitted to the RF receiver 50 only by wire, the number of channels is set to equal to or smaller than the input reception number of the RF receiver 50. In this configuration, the analogue MR signal transmitted in each channel and outputted to the RF receiver 50 as one signal is a signal including an MR signal of one coil element in some cases, and is a composite signal of MR signals of plural coil elements in other cases.

Each of the A/D converter 29a converts the analogue MR signals inputted from the RF coil device 100A into digital signals by using the direct sampling method, and inputs the digitized MR signals to the selecting circuit 29b. The above analogue MR signals are amplified by each of the preamplifiers 107 after being detected by each of the coil elements 106, and outputted to each of the A/D converters 29a via the cable 102, the connector 101 (see FIG. 3), and non-illustrated hard-wiring inside each of the connection ports 25.

Since the configuration of an A/D converter for the direct sampling method is simple in general, it is easy to enhance degree of integration of A/D converters for the direct sampling method. Thus, many A/D converters 29a can be included in each of the connection ports 25.

Since FIG. 5 shows a case where MR signals of six channels are outputted from the RF coil device 100A as an example, at least six A/D converters 29a are included in the digital processing circuit 29 of each of the connection ports 25 (only six A/D converters 29a are shown in FIG. 5 in order to avoid complication).

Actually, it is preferable that the A/D converters 29a whose number sufficiently covers the channel number of wearable type RF coil devices are included in the digital processing circuit 29 of each of the connection ports 25.

The number of the A/D converters 29a in each of the connection ports 25 is satisfactory, if it is not less than the number of coil elements of the RF coil device that has the maximum number of coil elements as a wearable type RF coil device capable of being connected to the MRI apparatus 10A, for example.

The selecting circuit 29b selects the MR signals of at least one channel, out of the digitized MR signals transmitted for each channel of the RF coil device 100A (in this example, six channels). More specifically, the selecting circuit 29b obtains a selection signal indicative of the channel(s) selected for imaging from the system control circuit 61, and thereby transmits only the MR signals of the selected channel(s) to the radio communication device 28.

Figure 6:
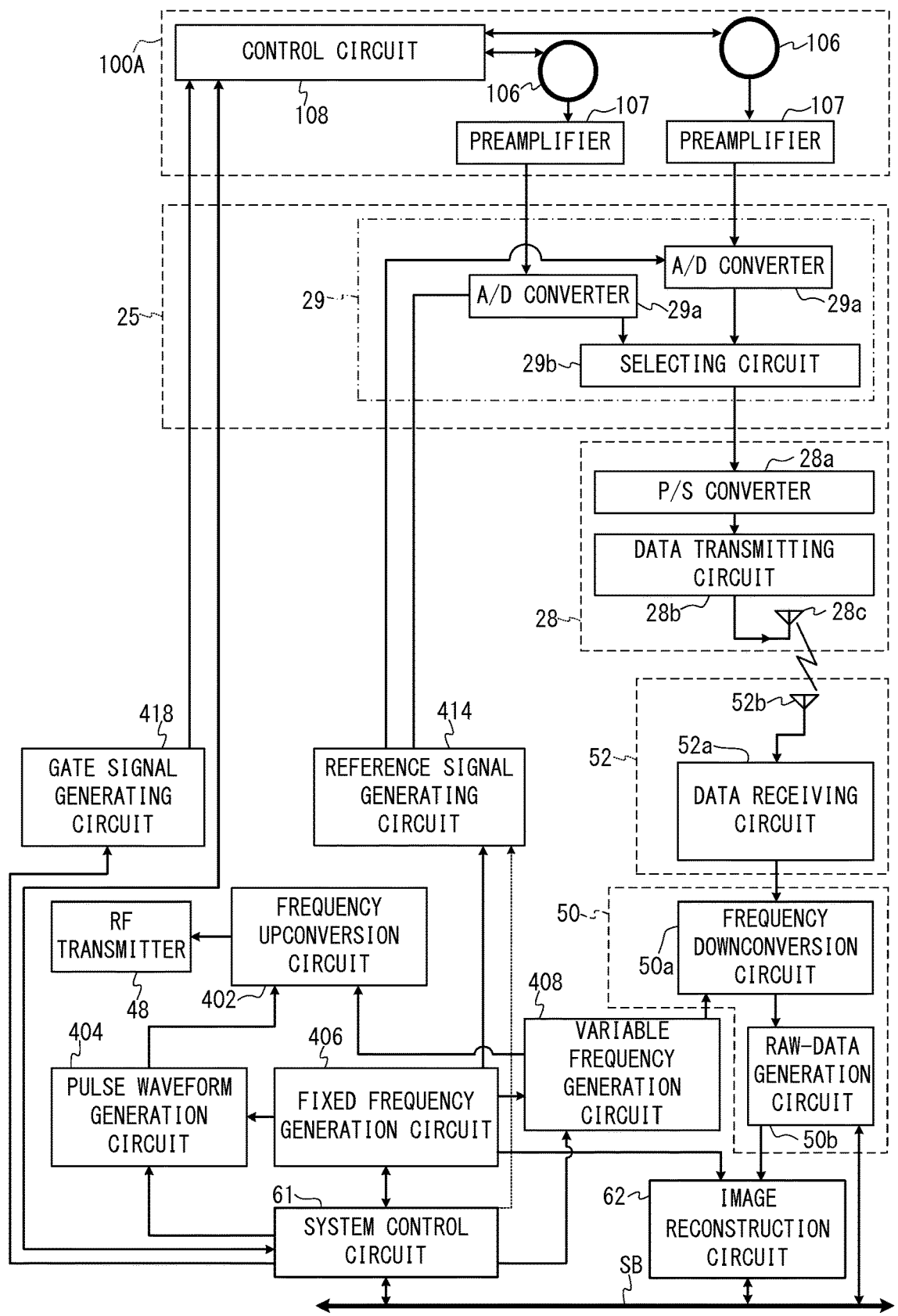
FIG. 6 is a schematic block diagram showing the configuration of the respective units relevant to digital radio communication system of the MR signals, in the MRI apparatus of the first embodiment.

FIG. 6 is a schematic block diagram showing the configuration of the respective components relevant to the digital radio communication system of the MR signals, in the MRI apparatus 10A of the first embodiment. Since it is complicated to show hard-wiring of all the coil elements 106, hard-wiring of connection destination of only two coil elements 106 as to the RF coil device 100A is shown and hard-wiring for the other coil elements 106 is omitted in FIG. 6.

As shown in FIG. 6, the radio communication device 28 includes a P/S (parallel/serial) converter 28a, a data transmitting circuit 28b, and an antenna 28c.

In addition, the control device 40 further includes a frequency upconversion circuit 402, a pulse waveform generation circuit 404, a fixed frequency generation circuit 406, a variable frequency generation circuit 408, a reference signal generation circuit 414, and a gate signal generation circuit 418, aside from the components shown in FIG. 1.

Moreover, the radio communication device 52 includes a data receiving circuit 52a and an antenna 52b.

Further, the RF receiver 50 includes a frequency downconversion circuit 50a and a raw-data generation circuit 50b.

The function of each of the above-described components will be explained as follows.

The fixed frequency generation circuit 406 generates a reference clock signal whose frequency is constant. The fixed frequency generation circuit 406 includes a crystal controlled oscillator with high degree of stability and so on, in order to generate the reference clock signal.

The fixed frequency generation circuit 406 outputs the reference clock signal to the reference signal generation circuit 414 and the variable frequency generation circuit 408. In addition, the fixed frequency generation circuit 406 outputs the reference clock signal to respective components performing clock synchronization inside the MRI apparatus 10A such as the image reconstruction circuit 62 and the pulse waveform generation circuit 404.

The variable frequency generation circuit 408 includes a PLL (Phase-Locked Loop), a DDS (Direct Digital Synthesizer), and a mixer. The variable frequency generation circuit 408 operates on the basis of the above reference clock signal.

The variable frequency generation circuit 408 generates a local signal (clock signal) of variable frequency which is equal to a setting value inputted from the system control circuit 61 as a center frequency of RF pulses.

In order to achieve the above operation, the system control circuit 61 outputs a default value of the center frequency of the RF pulses to the variable frequency generation circuit 408 before a prescan. In addition, the system control circuit 61 outputs a corrected value of the center frequency of the RF pulses to the variable frequency generation circuit 408 after the prescan.

The variable frequency generation circuit 408 outputs the above local signal of variable frequency to the frequency downconversion circuit 50a and the frequency upconversion circuit 402.

The system control circuit 61 acquires the identification information of the RF coil device 100A from the control circuit 108 of the RF coil device 100A via each of the connectors 37 and 27 of the gantry 30 side and the bed 20 side and at least one of the connection ports 25.

Thereby, the system control circuit 61 recognizes information on the RF coil devices such as information as to which of the various type of the RF coil devices is/are currently connected.

In addition, the system control circuit 61 determines the imaging conditions such as a repetition time, a type of RF pulses, a center frequency of the RF pulses, and a band width of the RF pulses in a pulse sequence, based on the imaging conditions entered by a user via the input device 72 (see FIG. 1). The system control circuit 61 outputs the imaging conditions determined in the above manner to the pulse waveform generation circuit 404.

The pulse waveform generation circuit 404 generates a pulse waveform signal of baseband by using the reference clock signal inputted from the fixed frequency generation circuit 406, depending on the imaging conditions inputted from the system control circuit 61. The pulse waveform generation circuit 404 outputs the pulse waveform signal of baseband to the frequency upconversion circuit 402.

The frequency upconversion circuit 402 multiplies the pulse waveform signal of baseband by the local signal inputted from the variable frequency generation circuit 408, then causes a desired signal band to pass by filtering, and thereby performs frequency conversion (upconversion). The frequency upconversion circuit 402 outputs the pulse waveform signal of baseband, whose frequency is up-converted, to the RF transmitter 48.

The RF transmitter 48 generates the RF pulses on the basis of the inputted pulse waveform signal.

The gate signal generation circuit 418 generates digital gate signals and transmits the gate signals to the control circuit 108 of the RF coil device 100A via the connectors 37 and 27 and at least one of the connection ports 25.

The gate signal is a control signal which switches an on/off state of each of the coil elements 106. As a switch changing the on/off state of each of the coil elements 106, for example, an active trap circuit 170 including such as a PIN diode (p-intrinsic-n Diode) is provided for each of the coil elements 106. The gate signal is a control signal of the above switch.

In a period during which RF pulses are transmitted to the object P, the gate signal inputted to the RF coil device 100A is set to on-level, for example. During the on-level period of the gate signal, the above switch becomes off-state so as to disconnect the loop of each of the coil elements 106 and thereby each of the coil elements 106 cannot detect MR signals. Thereby, coupling effect between the RF coil for transmitting RF pulses inside the RF coil unit 34 and each of the coil elements 106 for detecting MR signals is prevented.

On the other hand, except the period during which RF pulses are transmitted to the object P, the gate signal adjusted to off-level is wirelessly transmitted, for example. While the gate signal is off-level, the above switch becomes the on-state and each of the coil elements 106 can detect MR signals.

The reference signal generation circuit 414 generates a reference signal by performing various types of processing such as modulation, frequency conversion, amplification and filtering on the reference clock signal inputted from the fixed frequency generation circuit 406.

The reference signal is a sampling clock signal which synchronizes the RF coil device 100A as a transmission side of MR signals with a basic frequency of system based on the fixed frequency generation circuit 406.

In addition, the reference signal generation circuit 414 receives a trigger signal (A/D conversion start signal), which determines the sampling timing, from the system control circuit 61. The above sampling means, for example, to extract intensity of an analog signal at regular time intervals so that digital record is enabled.

Note that the trigger signal (A/D conversion start signal) as described below is superimposed on the reference signal received by the reference signal receiving circuit 218 at the start time of a scan.

As an example here, the reference signal generation circuit 414 outputs the reference signal and the trigger signal to each of the A/D converters 29a of the RF coil device 100A via the connectors 37 and 27 and at least one of the connection ports 25, by superimposing the trigger signal on the reference signal.

Next, the pathway of the MR signals will be explained.

More specifically, the analogue MR signals detected by each of the coil elements 106 are amplified by the corresponding preamplifier 107 as previously explained, then subjected to A/D conversion in the corresponding A/D converter 29a. At this time, each of the A/D converters 29a converts the inputted analogue MR signals into digital signals by the direct sampling method, by starting sampling and quantization based on the reference signal (sampling clock signal) in synchronization with the timing when the trigger signal is transmitted.

The digitized MR signals are outputted to the selecting circuit 29b, and the MR signals of only the coil element(s) 106 selected for imaging are transmitted from the selecting circuit 29b to the radio communication device 28.

The P/S converter 28a of the radio communication device 28 converts plural digitized MR signals from parallel signals into a serial signal for wireless transmission, and outputs the serial signal to the data transmitting circuit 28b. This is because the number of antenna for transmitting MR signals is only one (the antenna 28c) in the example of the present embodiment.

However, the present embodiment is not limited to the aspect of wirelessly transmitting MR signals as a serial signal. For example, MR signals may be wirelessly transmitted as parallel signals by increasing the number of antennas for transmitting and receiving MR signals.

The data transmitting circuit 28b generates MR signals for remote radio transmission (which are serial signals and digital signals) by performing processing such as error correction encoding, interleave, modulation, frequency conversion, amplification, and filtering on the inputted serial MR signals.

As to the radio communication frequency generated by the data transmitting circuit 28b, it is preferable to avoid frequencies which are equal to the number obtained by dividing a frequency of RF pulses (Larmor frequency) transmitted to the object P by a natural number (in the first embodiment, the carrier frequency is selected in this manner).

The data transmitting circuit 28b adjusts the power of the MR signals for wireless transmission to level appropriate for remote radio communication, and outputs the adjusted MR signals for wireless transmission to the antenna 28c. The antenna 28c radiates the electromagnetic wave of the MR signals.

The antenna 52b of the radio communication device 52 detects the carrier wave radiated from the antenna 28c, and outputs the detected carrier wave to the data receiving circuit 52a. The data receiving circuit 52a performs various types of processing such as amplification, frequency conversion, demodulation, deinterleave, and error correction decoding on the carrier wave of the MR signals inputted from the antenna 52b. Thereby, the data receiving circuit 52a extracts the original digitized MR signals from the MR signals for radio transmission, and outputs the extracted MR signals to the frequency downconversion circuit 50a of the RF receiver 50.

The frequency downconversion circuit 50a includes a mixer MX (see FIG. 9 as described below). The mixer MX multiplies the MR signals inputted from the data receiving circuit 52a by the local signal inputted from the variable frequency generation circuit 408. The frequency downconversion circuit 50a performs filtering in such a manner that a desired signal band of the MR signals outputted from the mixer MX gets through.

Thereby, the frequency downconversion circuit 50*a* performs thinning processing on the MR signals, and outputs the MR signals whose frequency is lowered to the raw-data generation circuit 50*b*. The above-described thinning processing means to perform frequency downconversion on the digitized high-frequency MR signals so that the MR signals fit the signal processing in the subsequent stage.

The raw-data generation circuit 50*b* generates raw data of the MR signals by performing predetermined signal processing on the above MR signals whose frequency is lowered. The raw data of the MR signals are inputted to the image reconstruction circuit 62, converted into k-space data in the image reconstruction circuit 62, and stored in the image reconstruction circuit 62.

Figure 7:
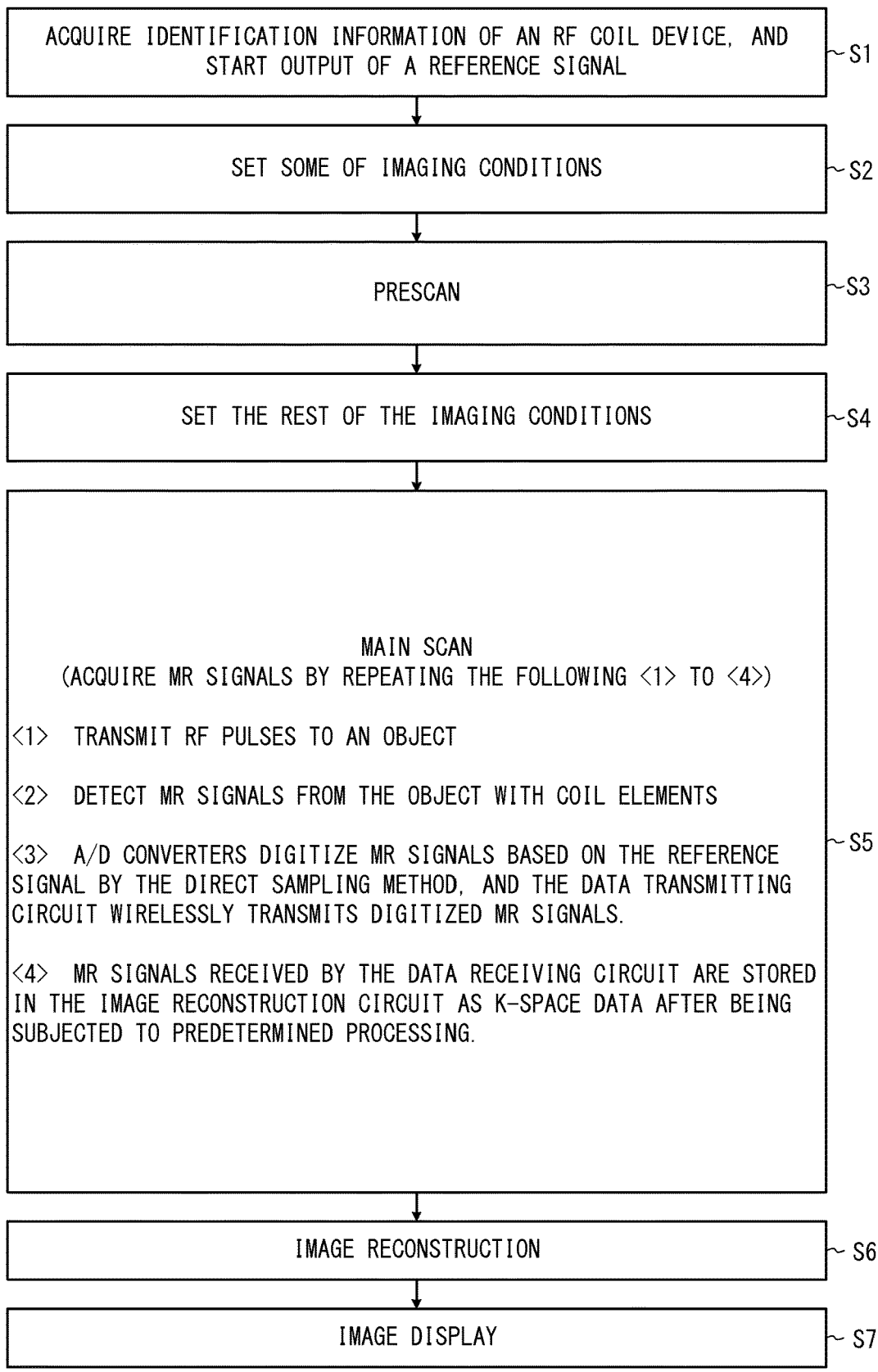
FIG. 7 is a flowchart illustrating an example of a flow of an imaging operation performed by the MRI apparatus of the first embodiment.

FIG. 7 is a flowchart illustrating an example of a flow of an imaging operation performed by the MRI apparatus 10A of the first embodiment. In the following, according to the step numbers in the flowchart shown in FIG. 7, an operation of the MRI apparatus 10A will be described by referring to the above-mentioned FIG. 1 to FIG. 6 as required.

[Step S1] The RF coil device 100A is set on the object P on the table 22, and the connector 101 of the RF coil device 100A is connected to one of the connection ports 25 (see FIG. 1). Thereby, the system control circuit 61 acquires the identification information of the RF coil device 100A, and recognizes that the RF coil device 100A is currently connected.

After recognizing the above identification information, the system control circuit 61 outputs further communication permission between the RF coil device 100A and the control device 40, and causes the control device 40 to supply electric power to the RF coil device 100A via the respective connectors 37 and 27 of the gantry 30 side and the bed 20 side, one of the connection ports 25, non-illustrated hard wiring.

In addition, the reference signal generation circuit 414 starts outputting the reference signal to each of the A/D converters 29*a* in accordance with the communication permission by the system control circuit 61 (the reference signal is continuously transmitted). Note that the trigger signal for determining the sampling timing is superimposed on the transmitted reference signal.

Moreover, the table driving structure 23 moves the table 22 into inside of the gantry 30 in accordance with the control signal inputted from the system control circuit 61. Afterward, the processing proceeds to the Step S2.

[Step S2] The system control circuit 61 sets some of the imaging conditions of the main scan based on the imaging conditions inputted to the MRI apparatus 10A via the input device 72 and the information on the currently used RF coil devices acquired in the Step S1 (in this example, information indicating that the RF coil devices 100A is used).

Afterward, the processing proceeds to the Step S3.

[Step S3] The system control circuit 61 causes the MRI apparatus 10A to perform prescans by controlling each component of the MRI apparatus 10A. In the prescans, for example, a corrected value of the center frequency of the RF pulses is calculated.

Afterward, the processing proceeds to the Step S4.

[Step S4] The system control circuit 61 sets the rest of the imaging conditions on the basis of the execution results of the prescans.

Afterward, the processing proceeds to the Step S5.

[Step S5] The system control circuit 61 causes the MRI apparatus 10A to perform the main scan by controlling each component thereof.

More specifically, electric currents are supplied from the shim coil power source 44 to the shim coil 32, and thereby the static magnetic field formed in the imaging space is uniformed.

Note that, during the implementation term of the main scan, the above-mentioned gate signal is continuously transmitted from the gate signal generation circuit 418 to the control circuit 108 of the RF coil device 100A.

Afterward, when the system control circuit 61 receives a command of start of imaging from the input device 72, the MR signals emitted from the object P are acquired by repeating the following processing composed of sub-steps <1> to <4> in series.

<1> The system control circuit 61 drives the gradient coil power source 46, the RF transmitter 48, and the RF receiver 50 in accordance with the pulse sequence, thereby the gradient magnetic fields are formed in the imaging region including the imaging part of the object P, and the RF pulses are transmitted from the RF coil unit 34 to the object P. Only during the transmission period of the RF pulses, the gate signal is set to, for example, on-level, and thereby each of the coil elements 106 of the RF coil device 100A becomes the off-state and the above-mentioned coupling effect is prevented.

<2> The gate signal is switched over to, for example, off-level after transmission of the RF pulses, and each of the coil elements 106 detects the MR signals caused by the nuclear magnetic resonance inside the object P.

Each of the analog MR signals detected by each of the coil elements 106 is amplified by each of the preamplifiers 107, and then outputted to each of the A/D converters 29*a* (see FIG. 6).

<3> Each of the A/D converter 29*a* starts sampling and quantization of the MR signals based on the reference signal in synchronization with the input timing of the trigger signal, and outputs the digitized MR signals to the selecting circuit 29*b*.

The selecting circuit 29*b* transmits the digitized MR signals from the coil elements 106 selected for imaging to the P/S converter 28*a* of the radio communication device 28.

The P/S converter 28*a* converts the inputted MR signals from parallel signals into a serial signal for wireless transmission, and outputs the serial signal to the data transmitting circuit 28*b*.

The data transmitting circuit 28*b* generates MR signals for radio transmission by performing the predetermined processing on the serial signal of the MR signals, and wirelessly transmits the serial signal from the antenna 28*c* to the antenna 52*b*.

<4> The data receiving circuit 52*a* extracts the original digitized MR signals by performing the predetermined processing on the MR signals for radio transmission, and outputs the extracted MR signals to the frequency downconversion circuit 50*a*.

The frequency downconversion circuit 50*a* performs frequency downconversion on the inputted MR signals, and outputs the MR signals whose frequency is lowered to the raw-data generation circuit 50*b*.

The raw-data generation circuit 50*b* generates raw data of the MR signals by performing the predetermined processing on the inputted MR signals. The raw data of the MR signals are outputted to the image reconstruction circuit 62, converted into k-space data, and stored in the image reconstruction circuit 62.

After completion of acquisition of the MR signals by repeating the above processing of the sub-steps <1> to <4>, the processing proceeds to the Step S6.

Incidentally, though the explanation is omitted in order to avoid complication, another (non-illustrated) digital processing circuit for the reception RF coil 24 is further disposed inside the table 22. Thus, the analogue MR signals outputted from the reception RF coil 24 inside the table 22 are also digitized under the direct sampling method by this digital processing circuit, then outputted to the radio communication device 28 and acquired in the similar manner (this point holds true for the next second embodiment).

[Step S6] The image reconstruction circuit 62 reconstructs image data by performing the image reconstruction processing including Fourier transformation etc. on the k-space data, and stores the reconstructed image data in the image database 63 (see FIG. 1).

Afterward, the processing proceeds to the Step S7.

[Step S7] The image processing circuit 64 obtains the image data from the image database 63 and generates display image data by performing the predetermined image processing on the obtained image data. The image processing circuit 64 stores the display image data in the memory circuit 76.

Then, the system control circuit 61 transmits the display image data to the display 74, and causes the display 74 to display images indicated by the display image data.

The foregoing is a description of the operation of the MRI apparatus 10A according to the first embodiment.

The difference between the first embodiment and conventional technology will be explained with reference to FIG. 8 and FIG. 9 as follows.

Figure 8:
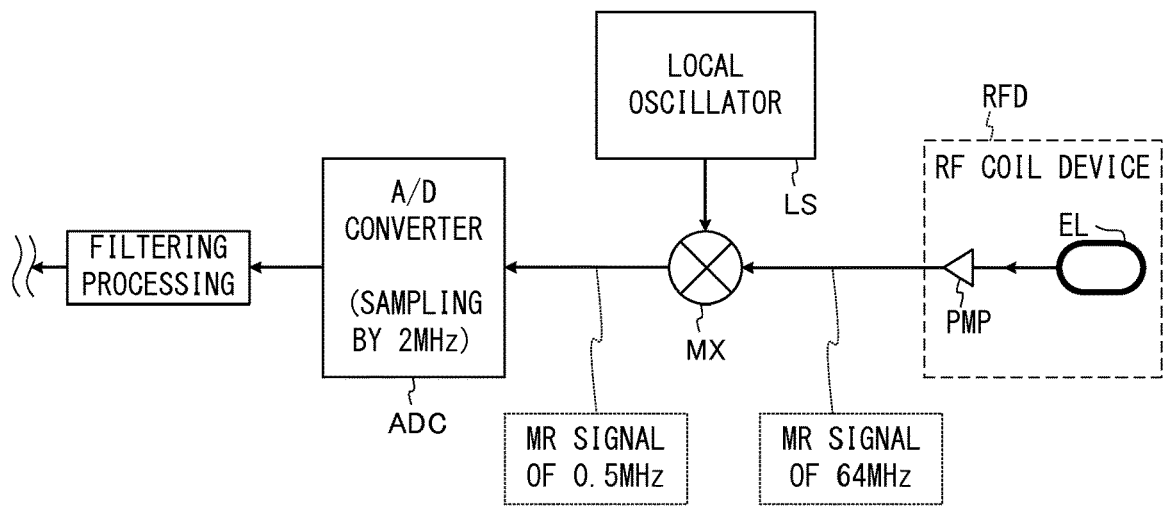
FIG. 8 is a block diagram of a reception system for the MR signals in which an A/D converter of conventional technology is used.

FIG. 8 is a block diagram of a reception system for the MR signals in which an A/D converter of conventional technology is used.

Figure 9:
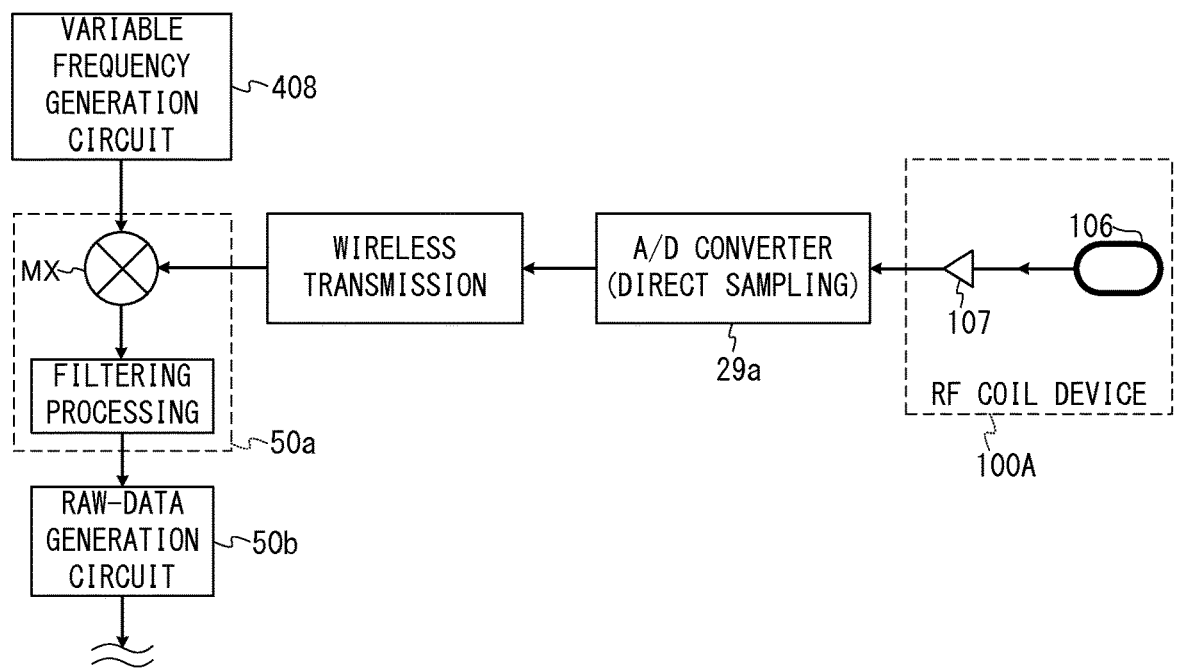
FIG. 9 is a block diagram of a reception system for the MR signals in which A/D conversion of the direct sampling method of the first embodiment is applied.

FIG. 9 is a block diagram of the reception system for the MR signals in which A/D conversion of the direct sampling method of the first embodiment is applied. The frequency of the MR signals detected by the RF coil device 100A is almost equal to the Larmor frequency and is a high frequency, for example, 64 MHz or 124 MHz.

As shown in FIG. 8, in the conventional technology, the high-frequency analogue MR signals detected by an coil element EL inside an RF coil device RFD is amplified by the preamplifier PMP. The high-frequency analogue MR signals outputted from the RF coil device RFD are subjected to frequency-downconversion processing so as to become, for example, 0.5 MHz, and then digitized by the A/D converter ADC.

Since the local oscillator and the mixer which perform the above frequency-downconversion processing are large in circuit size, it is difficult to include the A/D converter ADC inside a bed device in the conventional technology in which digitalization is performed after decreasing the frequency of the MR signals.

By contrast, in the first embodiment, the high-frequency analogue MR signals are amplified by the preamplifiers 107 inside the RF coil device 100A, as shown in FIG. 9 and FIG. 6. The high-frequency analogue MR signals outputted from the RF coil device 100A are digitized under the direct sampling method by the A/D converter 29a (for example, with a sampling frequency of 100 MHz or the like).

In this configuration, the A/D converter 29a can be included in each of the connection ports 25, because the local oscillator and the mixer are unnecessary as to A/D conversion and the A/D converters 29a are easily integrated because of their simple configuration. In the example of the first embodiment, the digitized high-frequency MR signals are wirelessly transmitted and then subjected to thinning processing (frequency downconversion) in the frequency downconversion circuit 50a of the RF receiver 50. After digitalization, frequency downconversion can be easily performed on the MR signals.

In a conventional MRI apparatus including the A/D converters whose number is not less than the minimum number of the necessary channels for the RF receiver in the rear stage, the input reception number of the RF receiver is less than the entire channel number of all the RF coil devices that can be simultaneously connected. Otherwise, the configuration of the RF receiver becomes complicated. Therefore, for example, a selecting circuit which selects some channels out of all the channels is disposed in the preceding stage of the RF receiver.

More specifically, in parallel imaging as an example, the respective RF coil devices for the head part, the chest part, the pelvic part, and the lower limbs are often concurrently attached on a patient in order to save time of reattaching the RF coil device. In this case, the number of all the coil elements of the four RF coil devices becomes, for example, 128. However, because the input reception number of the RF receiver is, for example, approximately 32 channels, a selection circuit which simply selects the analogue MR signals of 32 coil elements out of the 128 coil elements (without signal synthesis processing) is disposed between the RF receiver and each of the RF coil devices in the conventional technology.

In other word, in the conventional technology, because the MR signals are analogue signals before being inputted to the RF receiver and buffering (temporary storage) of the analogue MR signals cannot be performed, hardwiring is appropriately switched in such a manner that the MR signals transmitted from the coil element EL seamlessly flow to the rear stage on a real-time basis. As a result, the pathway in which the MR signals are transmitted in the state of analogue signals is longer in the conventional technology. The longer the pathway is, the more easily noise is mixed into the MR signals in the pathway.

By contrast, if the pathway in which the MR signals are transmitted in the state of analogue signals is shortened by digitizing the MR signals in the early stage (of the connection ports 25 in the table 22) like the first embodiment, intrusion of noise into the MR signals can be suppressed by a simple configuration.

In addition, because buffering of the MR signals can be performed in the early stage in the first embodiment, this makes the above selection circuit unnecessary and thus manufacturing cost is reduced.

Moreover, since it is easy to enhance integration degree of the A/D converters 29a of the direct sampling method due to their simple configuration, a large number of the A/D converters 29a can be included in each of the connection ports 25 in the first embodiment. Thus, the MR signals outputted from all the coil elements of all the RF coil devices, that can be concurrently connected to the MRI apparatus 10A, can be transmitted to the RF receiver 50 in the first embodiment. Accordingly, the MR signals can be effectively acquired in the first embodiment.

<Modifications of the First Embodiment>

Three modifications of the first embodiment will be explained as follows.

Firstly, in FIG. 1 and FIG. 2, an example in which the radio communication device 28 transmitting the MR signals is arranged on the side opposite to the gantry 30 in the supporting platform 21 and the radio communication device 52 receiving the MR signals is disposed to the wall of the imaging room has been explained. However, the arrangement of the radio communication devices 28 and 52 is not limited to the above aspect.

Figure 10:
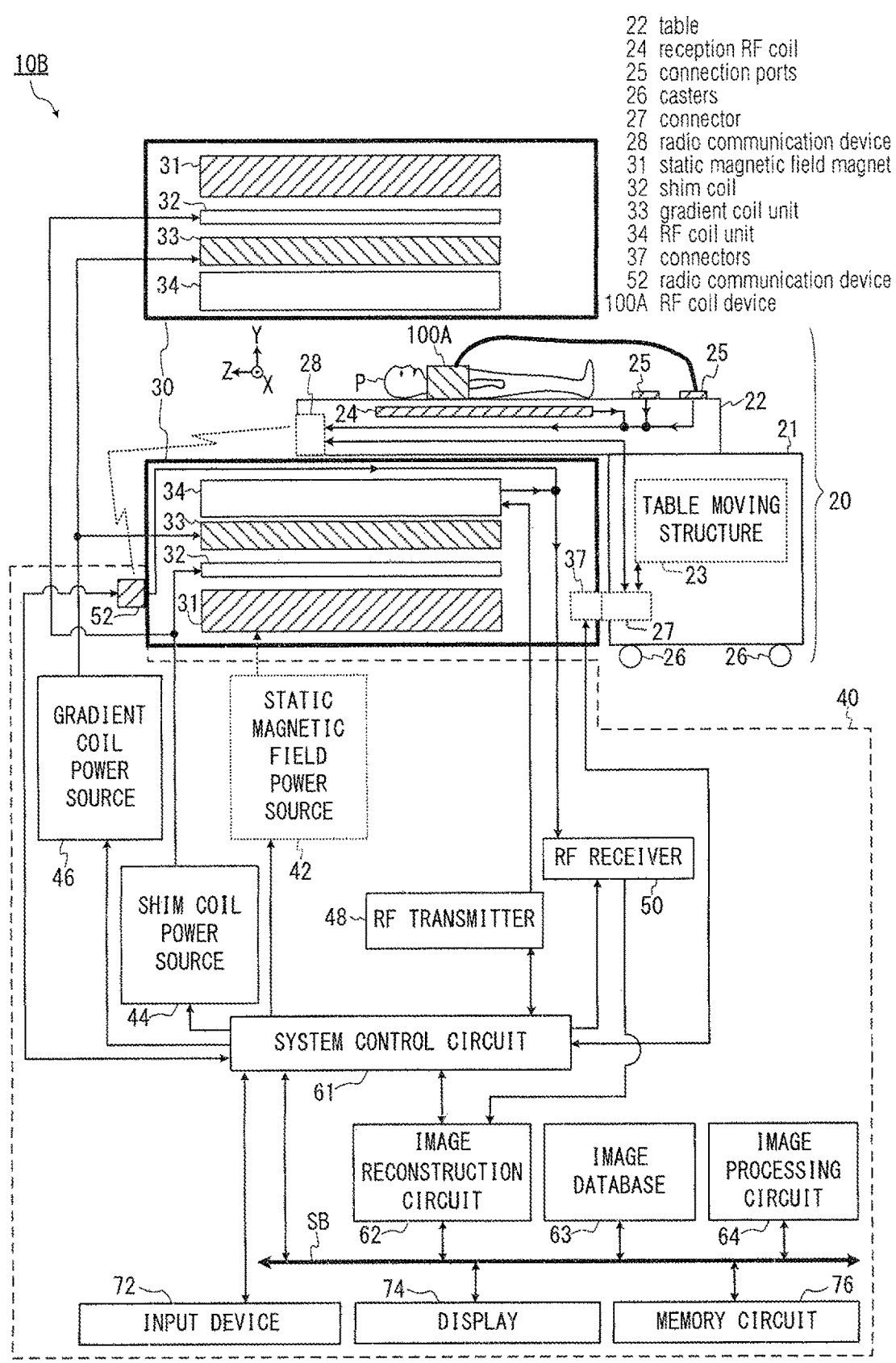
FIG. 10 is a block diagram showing an example of overall configuration of the first modification of the MRI apparatus of the first embodiment, in which the arrangement of the radio communication devices is changed.

FIG. 10 is a block diagram showing an example of the overall configuration of the first modification of the MRI apparatus 10B of the first embodiment, in which the arrangement of the radio communication devices 28 and 52 is changed. As shown in FIG. 10, the radio communication device 28 transmitting the MR signals may be arranged, for example, on the inner side of the gantry 30 in the table 22.

In this case, the radio communication device 52 receiving the MR signals is arranged, for example, on the side opposite to the supporting platform 21 in the exterior wall of the gantry 30.

Additionally, as to the arrangement position of the radio communication device 52 receiving the MR signals, it is preferable to avoid inside of the bore of the gantry 30 functioning as the imaging space in order to avoid influence on RF pulses or the like transmitted to the object P.

Moreover, the installation number of the radio communication device 52 is not limited to one. For example, plural radio communication devices 52 may be disposed to positions different from each other, and the strongest MR signal in intensity of reception radio waves received by one of the radio communication devices 52 may be outputted to the RF receiver 50.

Secondly, as the second modification, the arrangement of each digital processing circuit 29 is not limited to inside of each of the connection ports 25 of the table 22 like the above first embodiment but it may be arranged on the pathway from the RF coil device 100A to each of the connection ports 25.

In the second modification, a relay unit 160 which includes an A/D converter 166 is provided, and the RF coil device 100A is connected to one of connection ports 25' of a table 22' via the relay unit 160. The relay unit 160 may be interpreted as a part of the RF coil device 100A or interpreted as a part of the MRI apparatus.

The purpose of using the relay unit 160 is to digitize the MR signals in an earlier stage to obtain the same effect as the first embodiment even in the case of an MRI apparatus which does not include an A/D converter in each of the connection ports.

Figure 11:
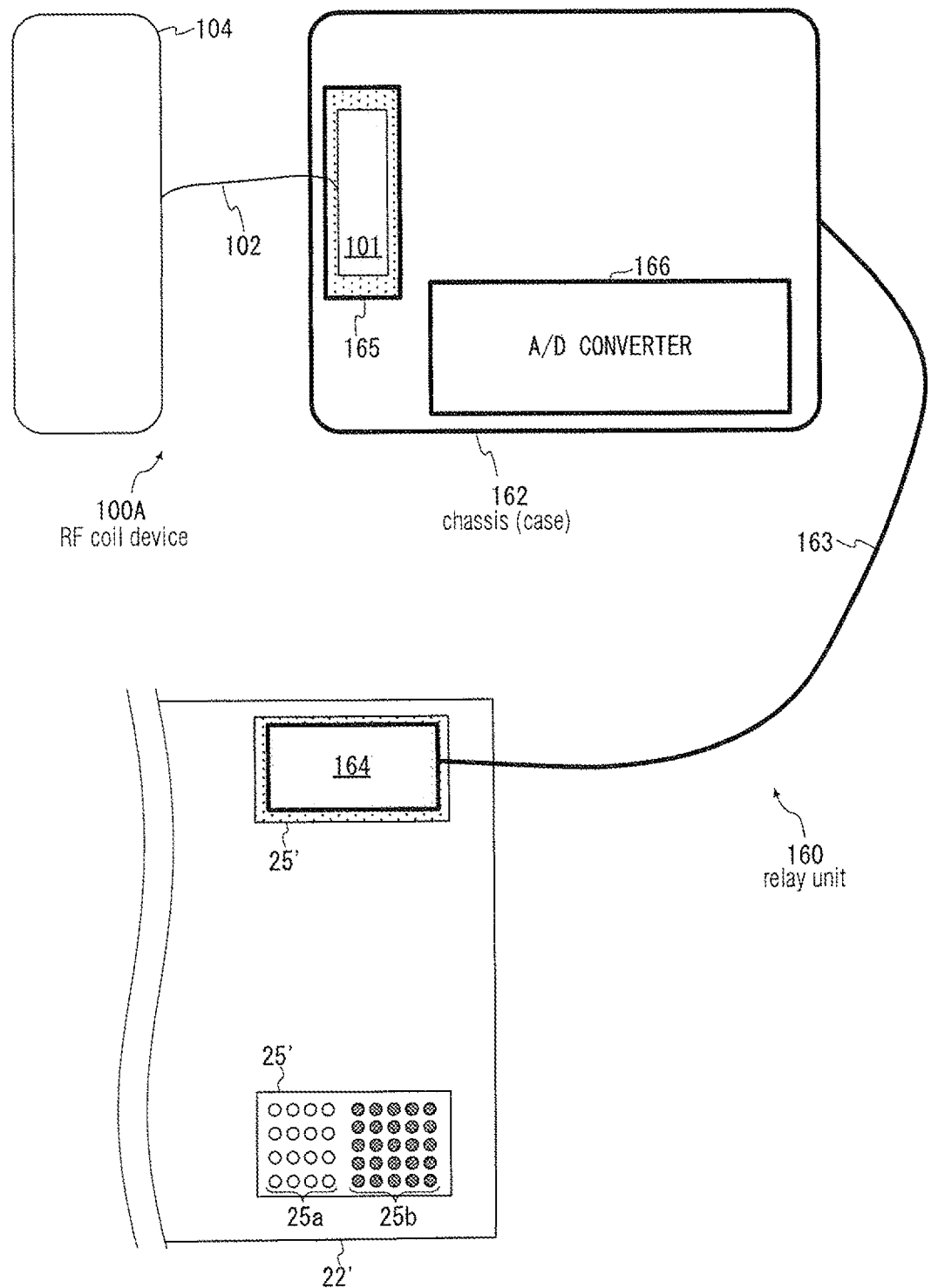
FIG. 11 is a schematic block diagram showing an example of the configuration and connection aspect of a relay unit of the second modification of the MRI apparatus of the first embodiment.

FIG. 11 is a schematic block diagram showing an example of the configuration and connection aspect of the relay unit 160 of the second modification of the first embodiment. As shown in FIG. 11, the relay unit 160 includes a chassis (case) 162, a cable 163 led from the chassis 162, and an output side connector 164 on the end of the cable 163. In FIG. 11, only the components of the relay unit 160 are indicated with bold lines for distinction.

The input side connector 165 is disposed on the chassis 162, and an A/D converter 166 having the same function as the A/D converter 29a of the first embodiment is included in the chassis 162.

The connector 101 of the RF coil device 100A is connected (interdigitated) with the input side connector 165. In addition, the output side connector 164 is connected (interdigitated) with one of the connection ports 25' of the table 22' of a non-illustrated conventional type of MRI apparatus.

As shown in the lower part of FIG. 11, each of the connection ports 25' of the table 22' of a non-illustrated conventional type of MRI apparatus includes plural MR signal sections 25a of 4-by-4 array and plural coil information sections 25b of 5-by-6 array, for example. The MR signal sections 25a are terminals which output the MR signals to the connection ports 25', and are coaxial connectors such as BNC (Bayonet Neill Concelman), for example. In addition, coil information sections 25b are terminals which output identification information of identifying an RF coil device to at least one of the connection ports 25'.

The (terminal of the) input side connector 165 of the relay unit 160 has the same size and shape as (the terminal of) the connection part of the connection port 25', and (the terminal of) the output side connector 164 has the same size and shape as (the terminal of) the connector 101. Thus, the relay unit 160 can be inserted in series between the RF coil device 100A of conventional type and the table 22' of conventional type.

As described above, in the second modification, an analogue MR signal can be converted into a digital signal by the relay unit 160 under the direct sampling method on the pathway from the RF coil device 100A to one of the connection ports 25', even in the case of the conventional type of the table 22' which does not include an A/D converter in each of the connection ports 25'.

In other words, analogue MR signals can be converted into digital signals in the pathway from the RF coil device 100A to one of the connection ports 25' without changing the specifications of the conventional bed and the conventional RF coil device. Thus, by separately connecting RF coil devices to the respective connection ports 25' via plural relay units 160, the same effect as the first embodiment can be obtained while reducing the manufacturing cost.

Thirdly, the MRI apparatus 10C of the third modification is configured so as to be sufficiently adaptive to both cases of using and omitting the above relay unit 160. More specifically, the bed of the MRI apparatus 10C of the third modification includes, for example, an interchangeability switching circuit inside its table or inside each of the connection ports.

Thus, the MRI apparatus 10C of the third modification is the same as the MRI apparatus 10A of the first embodiment except that the interchangeability switching circuit 180 is disposed, for example, inside each of the connection ports 25 instead of the digital processing circuit 29. Therefore, the overall configuration of the MRI apparatus 10C of the third modification is almost the same as FIG. 1 and duplicate explanation is omitted. In the following, the interchangeability switching circuit 180 will be explained.

Figure 12:
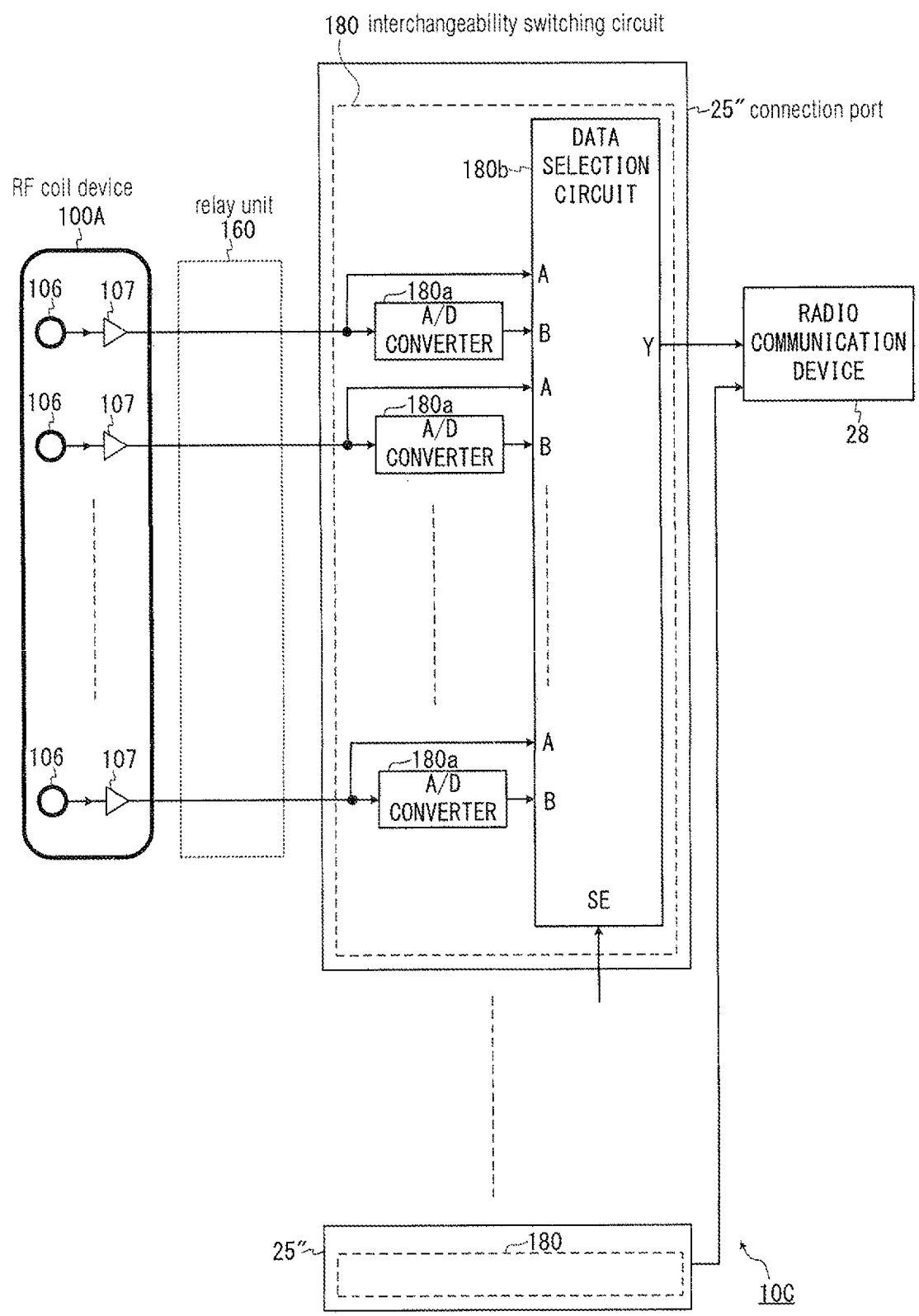
FIG. 12 is a schematic block diagram explaining functions of an interchangeability switching circuit of the third modification of the MRI apparatus of the first embodiment.

FIG. 12 is a schematic block diagram explaining the functions of the interchangeability switching circuit 180 of the third modification of the MRI apparatus 10C of the first embodiment. As shown in FIG. 12, the interchangeability switching circuit 180 includes plural A/D converters 180a and a data selection circuit 180b.

As to the explanation of an operation of the interchangeability switching circuits 180, it is divided into the first case in which the relay unit 160 is used and the second case in which the relay unit 160 is omitted.

As the first case, when a conventional RF coil device (such as 100A) without function of A/D conversion is directly connected to the connection port 25" of the MRI apparatus 10C, the system control circuit 61 outputs a selection control signal SE of, for example, off-level to the data selection circuit 180b via non-illustrated hard-wiring. When the selection control signal SE is off-level, the data selection circuit 180b transmits the MR signals inputted to the input B via the A/D converter 180a, to the radio communication device 28 from the output Y.

In this case, the MR signals digitized under the direct sampling method by the A/D converter 180a are outputted from the output Y. Note that, the interchangeability switching circuit 180 transmits only the MR signals from the coil elements 106 selected by the system control circuit 61 for detecting MR signals out of the digitized MR signals inputted from each of the A/D converters 180a, to the radio communication device 28.

As the second case, when a conventional RF coil device (such as 100A) without function of A/D conversion is connected to the connection port 25" of the MRI apparatus 10C via the relay unit 160, the system control circuit 61 outputs selection control signal SE of, for example, on-level to the data selection circuit 180b. When the selection control signal SE is on-level, the data selection circuit 180b outputs the MR signals inputted to the input A without going through the A/D converter 180a, from the output Y.

In this case, the MR signals digitized under the direct sampling method by the relay unit 160 are outputted from the output Y. Incidentally, the interchangeability switching circuit 180 transmits only the MR signals from the coil elements 106 selected by the system control circuit 61 for detecting MR signals out of the digitized MR signals inputted to each input A, to the radio communication device 28.

Note that, the input of the selection control signal SE may be manually performed by a user or it may be automatically performed based on whether or not the system control circuit 61 has acquired the identification information of the relay unit 160.

As described above, the third modification is sufficiently adaptive to both cases of using and omitting the relay unit 160, by installing the interchangeability switching circuit 180.

Moreover, by disposing the interchangeability switching circuits 180 inside the respective connection ports 25", the following effect can be obtained. That is, even if one of the connection ports 25" connected to an RF coil device without going through the relay unit 160 and another one of the connection ports 25" connected to an RF coil device via the relay unit 160 are mixed, MR signals appropriately digitized in accordance with each of the connection ports 25" can be transmitted to the radio communication device 28.

<The Second Embodiment>

The MRI apparatus 10D of the second embodiment is the advanced version of the first embodiment, and can use the following two types of RF coil devices. One of them is the conventional type of RF coil device 100A that is connected to one of the connection ports 25 of the table 22 and outputs analogue MR signals by wire. The other of them is an RF coil device 100B which digitizes received MR signals and wirelessly transmits the digitized MR signals.

Figure 13:
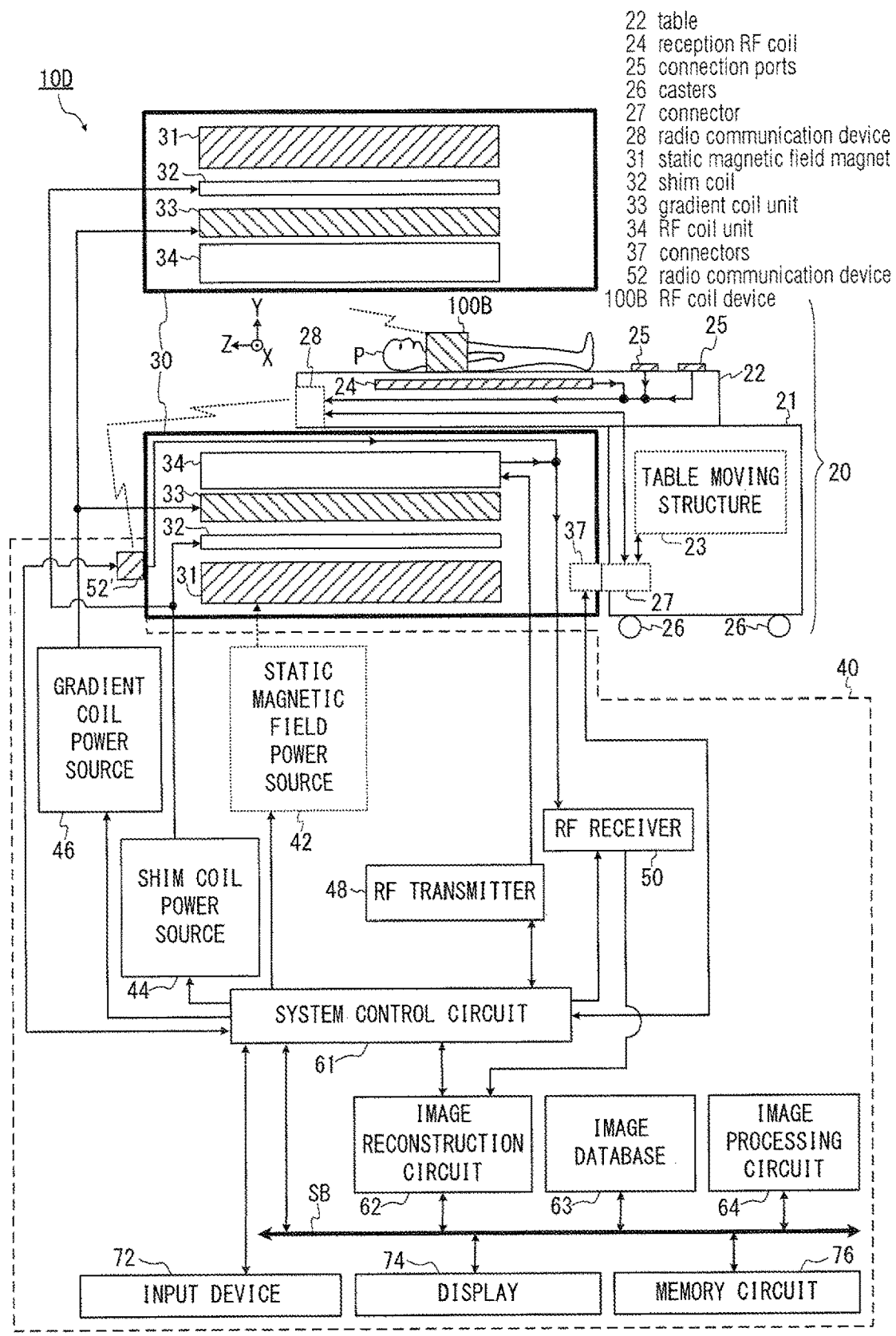
FIG. 13 is a block diagram showing an example of overall configuration of the MRI apparatus of the second embodiment.

FIG. 13 is a block diagram showing overall configuration of the MRI apparatus 10D of the second embodiment. The differences between the second embodiment and the first modification of the first embodiment shown in FIG. 10 are only the following two points.

The first point lies in that the RF coil device 100B is used in some cases as mentioned above. As to the RF coil device 100B, it will be explained with FIG. 14 below. Although FIG. 13 shows the case where the RF coil device 100B is used and the connection ports 25 are not used, one of the connection ports 25 is connected to the connector 101 in the above-mentioned manner when the RF coil device 100A is used.

The second point lies in that the MRI apparatus 10D includes a radio communication device 52' capable of receiving two types of digitized MR signals, instead of the radio communication device 52 of the MRI apparatus 10B in FIG. 10. One of the above two types of digitized MR signals is the digital MR signal obtained by performing the same signal processing as the first embodiment on the MR signal received by the RF coil device 100A and transmitted from the radio communication device 28. The other of the above two types of digitized MR signals is the digital MR signal directly wirelessly transmitted from the RF coil device 100B.

The radio communication device 52' receives the MR signals wirelessly transmitted from the radio communication device 28, when the radio communication device 52' acquires the identification information of the RF coil device 100A by wire from the RF coil device 100A via one of the connection ports 25.

In addition, the radio communication device 52' receives the MR signals directly wirelessly transmitted from the RF coil device 100B, in the case of wirelessly receiving the identification information of the RF coil device 100B from the RF coil device 100B.

Incidentally, though the radio communication device 52' is disposed on the exterior wall of the inner side of the gantry 30 to be exposed as an instance in FIG. 13, this is only an example. The radio communication device 52' may be disposed on the entrance of the gantry 30 where a projector and so on are arranged. Additionally or alternatively, the radio communication device 52' may be disposed on the wall or ceiling of the imaging room where the gantry 30 is installed.

Figure 14:
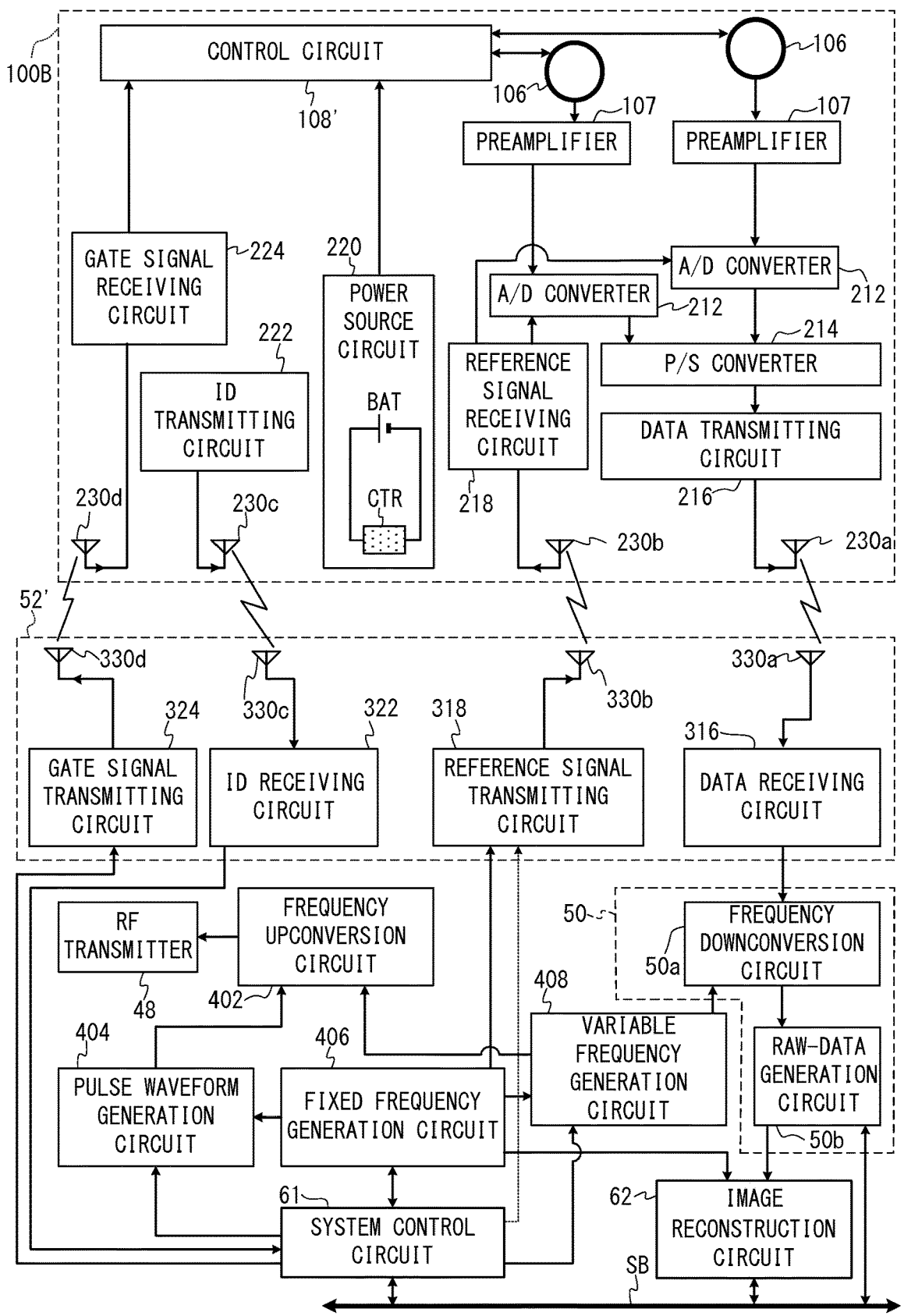
FIG. 14 is a block diagram showing an example of the configuration relevant to the digital radio communication system of the MRI apparatus of the second embodiment, in case where an RF coil device of wireless transmission type is applied.

FIG. 14 is a block diagram showing an example of the configuration relevant to the digital radio communication system of the MRI apparatus 10D of the second embodiment, when the RF coil device 100B of wireless transmission type is applied.

As shown in FIG. 14, the RF coil device 100B includes a control circuit 108', the coil elements 106, plural preamplifiers 107 corresponding to the respective coil elements 106, plural A/D converters 212 corresponding to the respective coil elements 106, a P/S converter 214, a data transmitting circuit 216, a reference signal receiving circuit 218, a power supply circuit 220, an ID (Identification Information) transmitting circuit 222, a gate signal receiving circuit 224, and the antennas 230a, 230b, 230c and 230d.

Although only two components are shown in FIG. 14 for the coil elements 106, the preamplifiers 107 and the A/D converter 212 in order to avoid complication, each number of these components may be three or more than three like the first embodiment.

The power supply circuit 220 includes a rechargeable battery BAT and a charging connector CTR. The charging connector CTR is connected to, for example, commercial power source or a charging adapter exclusively for the charging connector CTR. The charging connector CTR supplies a charging current to the rechargeable battery BAT.

Thus, though the rechargeable battery BAT of the RF coil device 100B is preliminarily charged before imaging as an example in the second embodiment, the MRI apparatus 10D and the RF coil device 100B may be configured so that the RF coil device 100B wirelessly receives electric power from the gantry 30 side. The rechargeable battery BAT supplies electric power to each component of the RF coil device 100B via non-illustrated hard-wiring during imaging.

The radio communication device 52' includes the data receiving circuit 316, the reference signal transmitting circuit 318, an ID (Identification Information) receiving circuit 322, a gate signal transmitting circuit 324, and antennas 330a, 330b, 330c and 330d.

Next, the four radio communication pathways between the RF coil device 100B and the radio communication device 52' will be explained by referring to functions of the respective components of the RF coil device 100B and the radio communication device 52'.

Firstly, in the pathway between the antennas 230c and 330c, the identification information of the RF coil device 100B is transmitted from the RF coil device 100B to the radio communication device 52'. More specifically, for example, the above identification information is stored in the ID transmitting circuit 222.

The ID transmitting circuit 222 generates carrier waves including the identification information of the RF coil device 100B for remote radio communication, and outputs the carrier waves to the antenna 230c. The antenna 230c radiates the inputted carrier waves to a space as electromagnetic waves.

The ID receiving circuit 322 outputs the identification information of the RF coil device 100B received by the antenna 330c to the system control circuit 61. Thereby, the system control circuit 61 recognizes information on which of various types of RF coil devices is currently connected or the like.

Secondly, in the pathway between the antennas 330d and 230d, the above-mentioned gate signal is wirelessly transmitted from the radio communication device 52' to the RF coil device 100B. More specifically, the gate signal transmitting circuit 324 generates the gate signal, then generates carrier waves including the gate signal for remote radio communication, and outputs the generated carrier waves to the antenna 330d. The antenna 330d radiates the inputted carrier waves to a space as electromagnetic waves. The gate signal receiving circuit 224 outputs the gate signal received by the antenna 230d to the control circuit 108'.

For the same reason as the first embodiment, while RF pulses are transmitted to the object P, the gate signal adjusted to on-level is wirelessly transmitted. Except in the span during which RF pulses are transmitted to the object P, the gate signal adjusted to off-level is wirelessly transmitted.

As another aspect of the second embodiment, a trigger signal may be transmitted from the gate signal transmitting circuit 324 to the gate signal receiving circuit 224 and the gate signal may be generated inside the gate signal receiving circuit 224 based on the trigger signal.

Thirdly, in the pathway between the antennas 330b and 230b, the reference signal on which the trigger signal is superimposed is wirelessly transmitted from the radio communication device 52' to the RF coil device 100B. More specifically, the trigger signal that determines the sampling timing in each of the A/D converters 212 is outputted from the system control circuit 61 to the reference signal transmitting circuit 318.

The reference signal transmitting circuit 318 generates the reference signal based on the reference clock signal inputted from the fixed frequency generating circuit 416 and receives the trigger signal from the system control circuit 61. The reference signal transmitting circuit 318 generates carrier waves including the trigger signal and the reference signal for remote radio communication, and outputs the generated carrier waves to the antenna 330b. The antenna 330b radiates the inputted carrier waves to a space as electromagnetic waves. The reference signal receiving circuit 218 outputs the trigger signal and the reference signal received by the antenna 230b to each of the A/D converters 212.

Fourthly, in the pathway between the antennas 230a and 330a, digitized MR signals are wirelessly transmitted from the RF coil device 100B to the radio communication device 52'.

More specifically, the number of the coil elements 106, the number of the preamplifiers 107, and the number of the A/D converters 212 are equal to each other inside the RF coil device 100B. In other words, each of the preamplifiers 107 corresponds to each of the coil elements 106, and each of the A/D converters 212 corresponds to each of the coil elements 106. Thus, the analogue MR signals detected by one or plural coil element(s) 106 selected for imaging are amplified by the corresponding preamplifier(s) 107, and then inputted to the corresponding A/D converter(s) 212.

Note that, as to selection of the above coil elements 106, the system control circuit 61 outputs a selection signal indicative of which of the coil elements 106 is/are selected to the gate signal transmitting circuit 324. The gate signal transmitting circuit 324 superimposes the selection signal on the gate signal before start of imaging, for example. Thereby, the control circuit 108' of the RF coil device 100B recognizes information on which of the coil elements 106 is/are selected.

The A/D converter 212 converts the analogue MR signals inputted from the preamplifiers 107 into digital signals by the direct sampling method. Here, each of the A/D converters 212 starts sampling and quantization of the MR signals based on the reference signal, in synchronization with the timing when the trigger signal is transmitted.

When at least one coil element 106 is not selected for imaging, the preamplifier 107 and the A/D converter 212 corresponding to the non-selected coil element(s) 106 do not operate as an example in the second embodiment.

Each of the A/D converters 212 outputs the digitized MR signal to the P/S converter 214. When at least two of the coil elements 106 are selected for imaging, the MR signals detected by these selected coil elements 106 and digitized by the A/D converters 212 are plural. In this case, the P/S converter 214 converts these plural MR signals from parallel signals into a serial signal for radio transmission, and outputs the serial signal to the data transmitting circuit 216.

However, the present embodiment is not limited to an aspect of transmitting the MR signals as a serial signal. For example, the MR signals may be wirelessly transmitted as parallel signals by increasing the number of antennas for transmitting and receiving MR signals.

The data transmitting circuit 216 generates the MR signal for remote radio transmission by performing the same processing as the first embodiment on the serial MR signal inputted from the P/S converter 214. The data transmitting circuit 216 outputs the MR signal for remote radio transmission to the antenna 230a.

The antenna 230a radiates the inputted MR signal for remote radio transmission to a space as electromagnetic waves. The frequency of the carrier waves radiated by the antenna 230a may be, for example, the same as the frequency of the carrier waves of the MR signals wirelessly transmitted from the antenna 28c of the radio communication device 28 in FIG. 15 as explained below.

The data receiving circuit 316 extracts the original digitized MR signals from the MR signals for remote radio transmission by performing the predetermined signal processing, and outputs the extracted MR signals to the frequency downconversion circuit 50a.

As to the frequency of the carrier waves for remote radio communication generated by the data transmitting circuit 216, the ID transmitting circuit 222, the reference signal transmitting circuit 318, and the gate signal transmitting circuit 324, it is preferable to avoid frequencies obtained by dividing the Larmor frequency by a counting number (the carrier frequency is selected in such a manner in the second embodiment).

In addition, the RF coil device 100B and the radio communication device 52' perform frequency separation of the carrier waves for remote radio communication. More specifically, the four frequencies of the respective carrier waves for remote radio communication generated by the data transmitting circuit 216, the ID transmitting circuit 222, the reference signal transmitting circuit 318, and the gate signal transmitting circuit 324 are set to values which are widely separated from each other.

Figure 15:
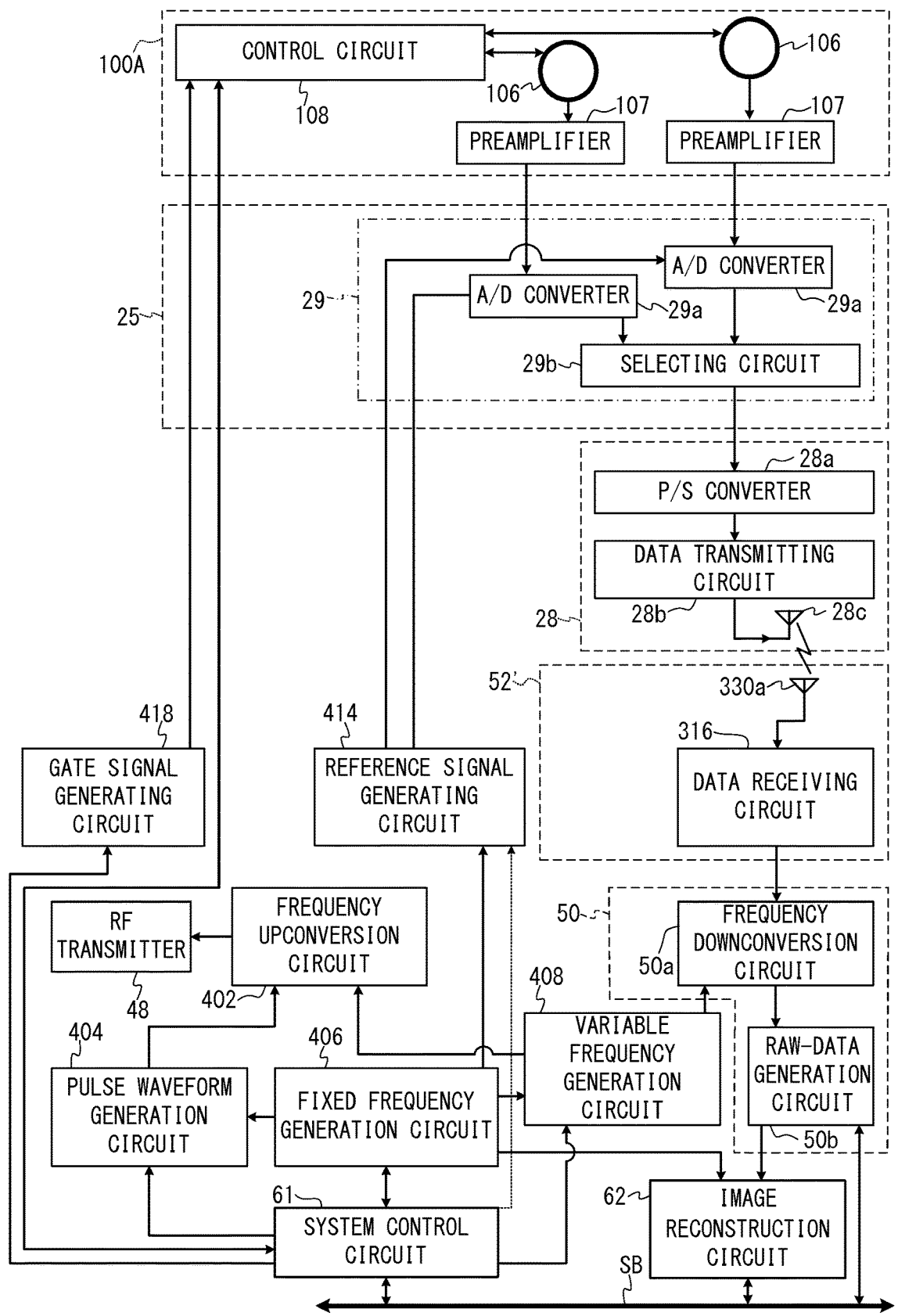
FIG. 15 is a block diagram showing an example of the configuration relevant to the digital radio communication system of the MRI apparatus of the second embodiment, in case where an RF coil device of wired transmission type is applied.

FIG. 15 is a block diagram showing an example of the configuration relevant to the digital radio communication system of the MRI apparatus 10D of the second embodiment, when the RF coil device 100A of wired transmission type is applied. In this case, the digital radio communication system of the MRI apparatus 10D is the same as the first embodiment, except that the antenna 330a and the data receiving circuit 316 of the radio communication device 52' function in a manner similar to the data receiving circuit 52a and the antenna 52b (FIG. 6) of the radio communication device 52 in the first embodiment.

Incidentally, the components (such as the reference signal transmitting circuit 318, the ID receiving circuit 322, the gate signal transmitting circuit 324, and the antennas 330b, 330c and 330d) inside the radio communication device 52' that do not function in the case of using the RF coil device 100A are omitted in FIG. 15 in order to avoid complication.

Figure 16:
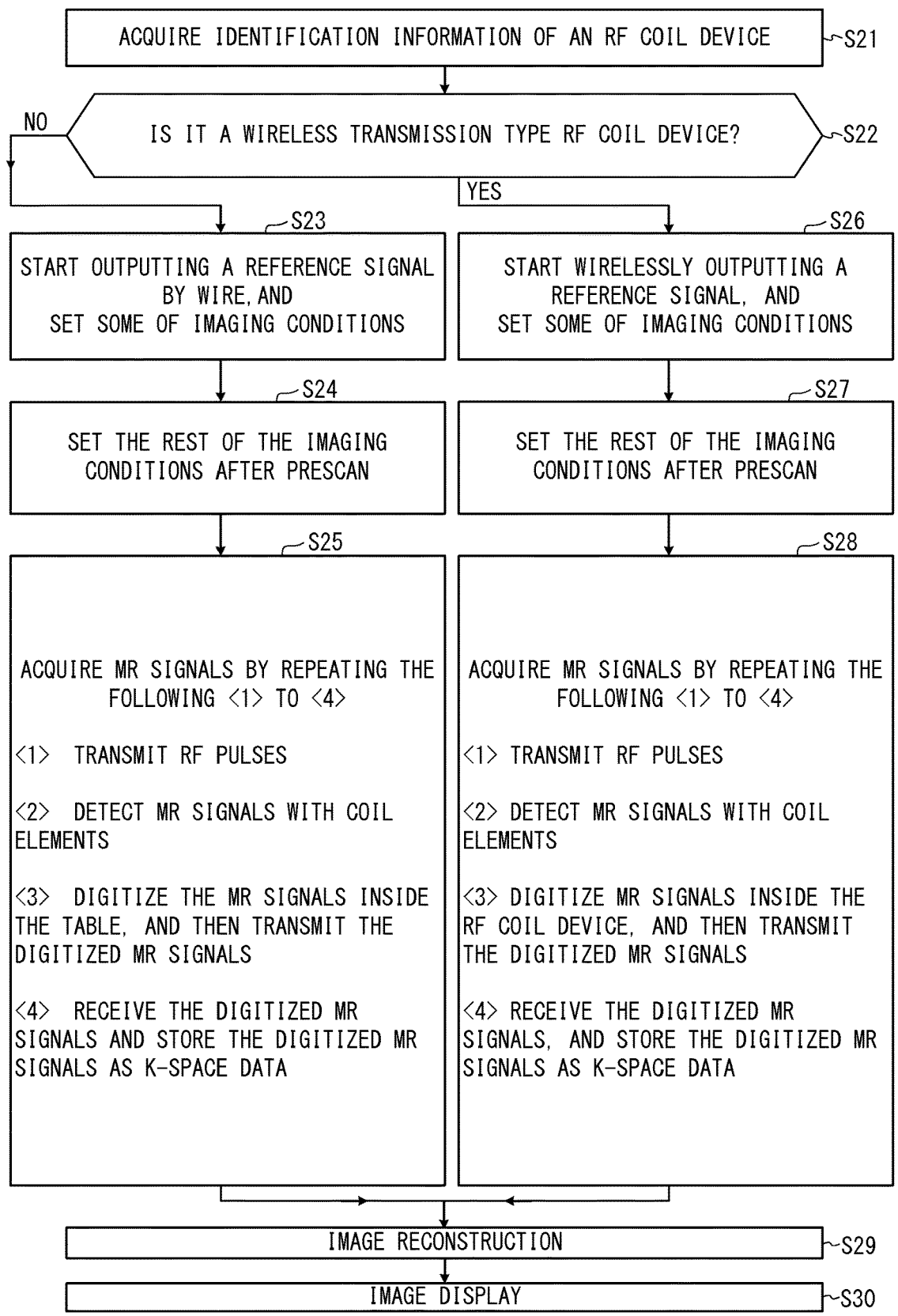
FIG. 16 is a flowchart illustrating an example of a flow of an imaging operation performed by the MRI apparatus of the second embodiment.

FIG. 16 is a flowchart illustrating an example of a flow of an imaging operation performed by the MRI apparatus 10D of the second embodiment. In the following, according to the step numbers in the flowchart shown in FIG. 16, an operation of the MRI apparatus 10D will be described by referring to the above-mentioned FIG. 13 to FIG. 15 as required.

[Step S21] As an example here, it is assumed that the RF coil device 100A or the RF coil device 100B is attached on the object P on the table 22. The system control circuit 61 acquires the identification information of the RF coil device.

When the RF coil device 100A is attached, the identification information of the RF coil device 100A is inputted by wire into the system control circuit 61 via one of the connection ports 25 in the way similar to the first embodiment (see FIG. 15).

By contrast, when the RF coil device 100B is attached, the system control circuit 61 acquires the identification information of the RF coil device 100B wirelessly transmitted between the antenna 230c and the antenna 330c from the radio communication device 52', as previously explained (see FIG. 14).

Thereby, the system control circuit 61 recognizes which of the RF coil devices is currently attached, and outputs further communication permission between the recognized RF coil device and the control device 40.

Afterward, the processing proceeds to the Step S22.

[Step S22] When the RF coil device 100A is attached, the system control circuit 61 controls each component so that each component supplies electric power to the RF coil device 100A in the way similar to the first embodiment, and the table moving structure 23 moves the table 22 into inside of the gantry 30 in the previously mentioned manner.

Afterward, the processing proceeds to the Step S23.

On the other hand, when the RF coil device 100B is attached, the table moving structure 23 moves the table 22 into inside of the gantry 30 in the previously mentioned manner, and then the processing proceeds to the Step S26.

[Step S23] The reference signal generation circuit 414 starts outputting the reference signal to the A/D converters 29a by wire in the way similar to the first embodiment (the reference signal is continuously transmitted). Incidentally, the trigger signal is superimposed on the reference signal.

The system control circuit 61 sets some of the imaging conditions of the main scan, based on the imaging conditions inputted to the MRI apparatus 10D via the input device 72 and the information on the currently used RF coil device acquired in the Step S21.

Afterward, the processing proceeds to the Step S24.

[Step S24, S25] The processing of the Step S24 is similar to the Step S3 and the Step S4 of FIG. 7 in the first embodiment. The processing of Step S25 is similar to the Step S5 of the first embodiment.

Afterward, the processing proceeds to the Step S29.

[Step S26] As explained with FIG. 14, the reference signal, on which the trigger signal is superimposed, is wirelessly transmitted from the reference signal transmitting circuit 318 of the radio communication device 52' to the reference signal receiving circuit 218 of the RF coil device 100B, and further outputted to each of the A/D converters 212. The system control circuit 61 sets some of the imaging conditions of the main scan in the way similar to the Step S23.

Afterward, the processing proceeds to the Step S27.

[Step S27] Prescans are performed in the way similar to the Step S3 and the Step S4 of the first embodiment, and the system control circuit 61 sets the rest of the imaging conditions of the main scan based on the execution results of the prescans.

Afterward, the processing proceeds to the Step S28.

[Step S28] The system control circuit 61 causes each component of the MRI apparatus 10D to perform the main scan in which the MR signals are directly wirelessly received from the RF coil device 100B. More specifically, the static magnetic field formed in the imaging space is uniformed by the shim coil 32 (FIG. 13) in the same way as mentioned above.

During implementation term of the main scan, the gate signal is continuously transmitted from the gate signal transmitting circuit 324 (FIG. 14) to the control circuit 108' of the RF coil device 100B. Incidentally, before the main scan, the gate signal on which the selection signal is superimposed is wirelessly transmitted.

After this, when the system control circuit 61 receives a command of start of imaging from the input device 72, the MR signals emitted from the object P are acquired by repeating the processing composed of the following substeps <1> to <4> in series.

<1> The system control circuit 61 controls each component of the MRI apparatus 10D in a similar manner as described above, so that the gradient magnetic fields are formed and RF pulses are transmitted to the object P. Only during the transmission period of the RF pulses, the gate signal is set to, for example, on-level.

<2> The gate signal is switched over to, for example, off-level after transmission of the RF pulses, and each of the coil elements 106 detects the MR signals caused by the nuclear magnetic resonance inside the object P. Each of the detected analogue MR signals is amplified by the corresponding preamplifier 107, and then inputted into the corresponding A/D converter 212.

<3> Each of the A/D converters 212 corresponding to the selected coil elements 106 for imaging indicated by the selection signal starts sampling and quantization of the MR signals by the direct sampling method based on the reference signal, in synchronization with the timing when the trigger signal is wirelessly transmitted. Each of the A/D converters 212 outputs the digitized MR signals to the P/S converter 214.

The P/S converter 214 converts the inputted digital MR signals from parallel signals into a serial signal for wireless transmission, and outputs the serial signal to the data transmitting circuit 216. The data transmitting circuit 216 generates a serial signal of the MR signals for radio transmission in the previously mentioned manner, and wirelessly transmits the generated serial signal for radio transmission from the antenna 230a to the antenna 330a.

<4> The data receiving circuit 316 of the radio communication device 52' extracts the original digital MR signals by performing the predetermined processing on the serial signal for radio transmission received by the antenna 330a. The data receiving circuit 316 outputs the extracted MR signals to the frequency downconversion circuit 50a. Afterward, raw data of the MR signals are converted into k-space data and the k-space data are stored in the image reconstruction circuit 62, in the way similar to the first embodiment.

After completion of acquisition of the MR signals by repeating the processing of the above sub-steps <1> to <4>, the processing proceeds to the Step S29.

[Step S29, S30] The processing of the Steps S29 and S30 is similar to the processing of the Steps S6 and S7 in FIG. 7 of the first embodiment. The foregoing is a description of the operation of the MRI apparatus 10D of the second embodiment.

As described above, the same effects as the first embodiment can be obtained in the second embodiment.

Moreover, in the second embodiment, the radio communication device 52' can receive (a) the MR signals directly wirelessly transmitted from the RF coil device 100B and (b) the MR signals transmitted by wire from the RF coil device 100A, then digitized inside the table 22 and then wirelessly transmitted from the radio communication device 28. Thus, the MRI apparatus 10D of the second embodiment can use both of the conventional type of RF coil device 100A that outputs the analogue MR signals by wire and the RF coil device 100B that wirelessly transmits digital MR signals.

Two points are complemented as to the second embodiment as follows.

Firstly, in the second embodiment, the control device 40 side of the MRI apparatus 10D receives the identification information of an RF coil device by wire or wirelessly, and then automatically selects transmission system of MR signals by the radio communication device 52' or the like based on the identification information. However, embodiments of the present disclosure are not limited to such an aspect. Each component of the MRI apparatus may be configured so that a user can manually input the connection information of RF coil devices (including the identification information) and the control device 40 side automatically selects the reception aspect of MR signals based on the inputted connection information.

Secondly, an example in which only either (a) the MR signals directly wirelessly transmitted from the RF coil device 100B or (b) the MR signals wirelessly transmitted from the radio communication device 28 after being transmitted from the RF coil device 100A by wire and digitized inside the table 22 are received by the radio communication device 52' has been explained. This is only an example for simplifying the explanation.

For example, plural RF coil devices, whose transmission aspects are different from each other, may be separately attached on plural parts of the object P. As a concrete example of this case, the RF coil device 100A of cable type may be attached on the chest part and an RF coil device that digitizes MR signals and wirelessly transmits the digitized MR signals may be attached on the abdominal part, at the same time. In this case, the MR signals outputted from the RF coil device 100A are acquired under the processing of the above Steps S23 to S25, and the MR signals wirelessly transmitted from the RF coil device attached on the abdominal part are acquired under the processing of the above Steps S26 to S28.

<The Third Embodiment>

In the third embodiment, the technology of the first embodiment is applied to a novel technology in which MR signals are wirelessly transmitted via an induced electric field by proximity wireless communication.

Figure 17:
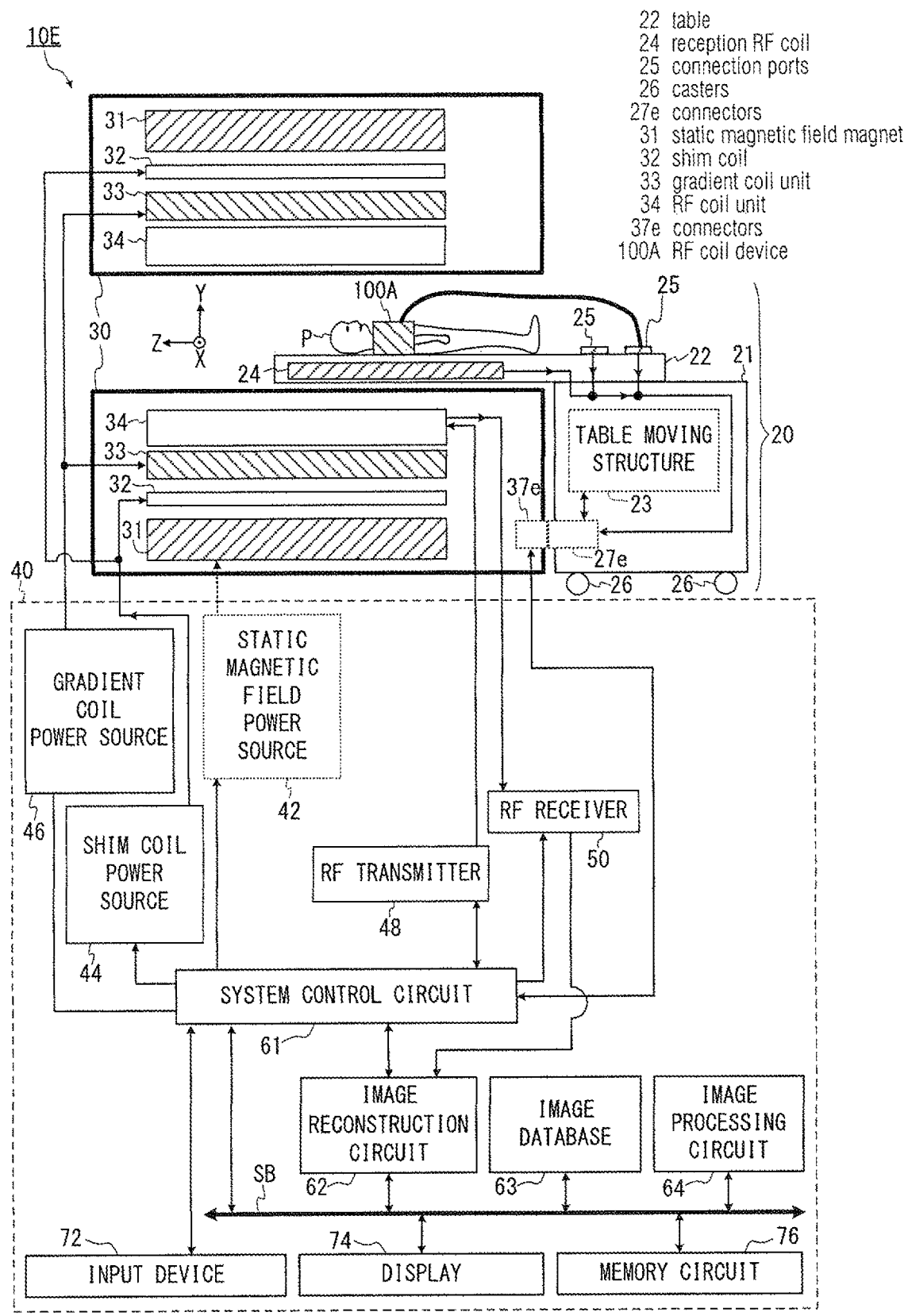
FIG. 17 is a block diagram showing an example of overall configuration of the MRI apparatus of the third embodiment.

FIG. 17 is a block diagram showing overall configuration of the MRI apparatus 10E of the third embodiment. The differences between this MRI apparatus 10E shown in FIG. 17 and the MRI apparatus 10A of the first embodiment shown in FIG. 1 are only the following two points.

Firstly, since remote wireless communication of MR signals is not performed, the radio communication devices 28 and 52 of the first embodiment are omitted.

Secondly, the configuration of the connector 27e of the bed 20 and the connector 37e of the gantry 30 are different from the configuration of the connectors 27 and 37 of the first embodiment. More specifically, in the pathway between the connectors 27e and 37e, the MR signals received by the RF coil device 100A and the reception RF coil 24 are wirelessly transmitted via an induced electric field by proximity wireless communication. Additionally, in the pathway between the connectors 27e and 37e, transmission of the control signals to the table moving structure 23 and the RF coil device 100A and electric power supply are performed in the way similar to the first embodiment.

Figure 18:
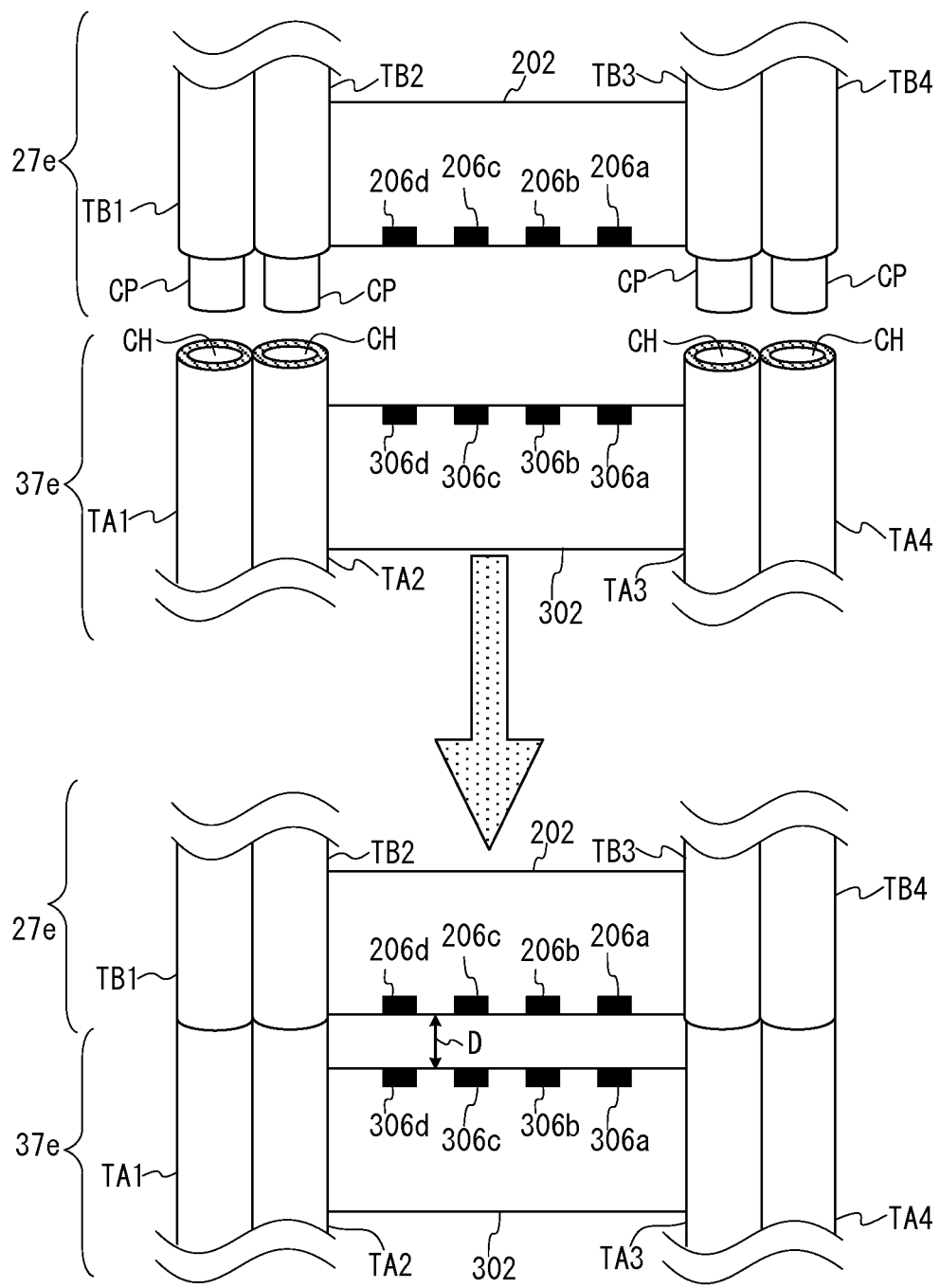
FIG. 18 is a schematic diagram showing an example of a linking aspect of connecting the connector of the bed with the connector of the gantry, in the MRI apparatus of the third embodiment.

FIG. 18 is a schematic diagram showing an example of a linking aspect of connecting the connector 27e of the bed 20 with the connector 37e of the gantry 30, in the MRI apparatus 10E of the third embodiment. The upper part of FIG. 18 indicates the state before coupling fixture, and the lower part of FIG. 18 indicates the state in which both sides are coupled and fixed (so as to be electrically connected with each other).

As shown in the upper part of FIG. 18, the connector 37e of the gantry 30 includes a chassis 302 and terminals TA1, TA2, TA3 and TA4 on the ends of respective cables. Each of the terminals TA1 to TA4 is formed of conductor, and the tip of each of the terminals TA1 to TA4 has a connection port (connection hole) CH.

In addition, the connector 27e of the bed 20 includes a chassis 202 and terminals TB1, TB2, TB3 and TB4 on the ends of the respective cables. Each of the terminals TB1 to TB4 is formed of conductor, and the tip of each of the terminals TB1 to TB4 has a protrusion (connection port) CP.

Each of the chassis 202 and 302 functions as a radio communication device, as described below.

The connectors 27e and 37e are detachably fixed to each other by interdigitating the protrusion CP of each of the terminals TB1 to TB4 with the connection port CH of each of the terminals TA1 to TA4.

The cable of the gantry 30 side and the bed 20 side coupled by interdigitating the terminal TA1 with the terminal TB1 is a cable for supplying electric power from the gantry 30 side to the bed 20 side, for example.

The cable of the gantry 30 side and the bed 20 side coupled by interdigitating the terminal TA2 with the terminal TB2 is a cable for communication of the control signals between the system control circuit 61 and the table moving structure 23, for example.

The cable of the gantry 30 side and the bed 20 side coupled by interdigitating the terminal TA3 with the terminal TB3 and the cable of the gantry 30 side and the bed 20 side coupled by interdigitating the terminal TA4 with the terminal TB4 are cables for other control signals.

Although only four cables are shown for each of the bed 20 side and the gantry 30 in FIG. 18 in order to avoid complication, actually further cables are coupled to each other, for example.

In addition, the above interdigitation is only an example of coupling the connectors 27e and 37e, and other detachable methods of coupling and fixing both sides may be used.

As shown in the lower part of FIG. 18, the interval between the chassis 302 and 202 becomes D in the state of being coupled and fixed to each other. This interval D is an interval in which radio communication via an induced electric field is practicable. Antennas 206a, 206b, 206c and 206d for the radio communication via an induced electric field are buried inside the chassis 202, and antennas 306a, 306b, 306c and 306d for the radio communication via an induced electric field are buried inside the chassis 302.

The antennas 206a to 206d are disposed so as to face the antennas 306a to 306d, respectively, in the above coupled and fixed state.

The short-distance radio communication via an induced electric field is performed on the pathway between the chassis 302 and the chassis 202. An induced electric field means an electric field caused by time change of magnetic flux density. As the short-distance radio communication via an induced electric field, for example, TransferJet (Trademark) which uses an induced electric field combined coupler as an antenna can be used.

More specifically, the induced electric field combined coupler includes a coupling electrode, a resonance stub, a ground, and so on (not shown). If an electric signal is inputted to the resonance stub of the transmission side, electric charges are accumulated in the coupling electrode, and virtual electric charges equal to the electric charges accumulated in the coupling electrode are generated in the ground. Thereby, a micro electrical dipole is composed by these electric charges, and this micro electrical dipole functions as a transmission side antenna. In other words, data are transmitted to the receiving side via an induced electric field of a longitudinal wave generated by the micro electrical dipole. Since a longitudinal wave vibrating in parallel with the traveling direction is not influenced by the direction of an antenna, stable data transmission can be achieved.

However, if the receiving side is separated from the transmission side beyond limit, both sides are not electro-magnetically coupled and data transmission cannot be performed. This is because induced electric fields formed by the induced electric field combined couplers rapidly attenuate if the interval between both sides of the couplers becomes distant.

Although the antennas 206a to 206d are discretely disposed and the antennas 306a to 306d are discretely disposed in order to distinguish respective components in FIG. 18, interference between each of the four radio communication pathway can be avoided without arranging them separately.

More specifically, the four radio frequencies used in the pathway of the antennas 206a to 306, the pathway of the antennas 206b to 306b, the pathway of the antennas 206c to 306c, and the pathway of the antennas 206d to 306d may be separated (these four frequency values may be widely set apart). As to the radio communication frequency, it is preferable to avoid frequencies which are equal to the number obtained by dividing a center frequency of RF pulses transmitted to the object P by a natural number, in each of the radio communication pathway.

It is preferable that the buried depth of each of the antennas 206a to 206d inside the chassis 202 and the antennas 306a to 306d inside the chassis 302 is such a depth that both antennas are electro-magnetically coupled and radio communication via an induced electric field is sufficiently practicable.

If buried depth is too deep, the interval D (see the lower part of FIG. 18) between the transmission side and the receiving side cannot become close enough to electro-magnetically couple the antennas 206a to 206d of the transmission side with the antennas 306a to 306d of the receiving side. In this case, the radio communication via an induced electric field will be difficult.

As long as an electric dipole (antenna) of the chassis 202 side is not directly contacted to an electric dipole (antenna) of the chassis 302 side, the chassis 202 may be contacted to the chassis 302 (the distance between the surface of the chassis 202 and the surface of chassis 302 may be zero). This is because it is enough if the interval D causing an induced electric field is kept between the antennas of the transmission side and the antennas of the receiving side.

In addition, if imaging time is long, for example, 30 minutes, transmission span of the MR signals becomes long. During the transmission span, it is preferable to fix the transmission side and the receiving side each other so as not to jolt out of alignment. Thus, configuration of infallibly fixing the transmission side and the receiving side like the present embodiment is preferable.

Figure 19:
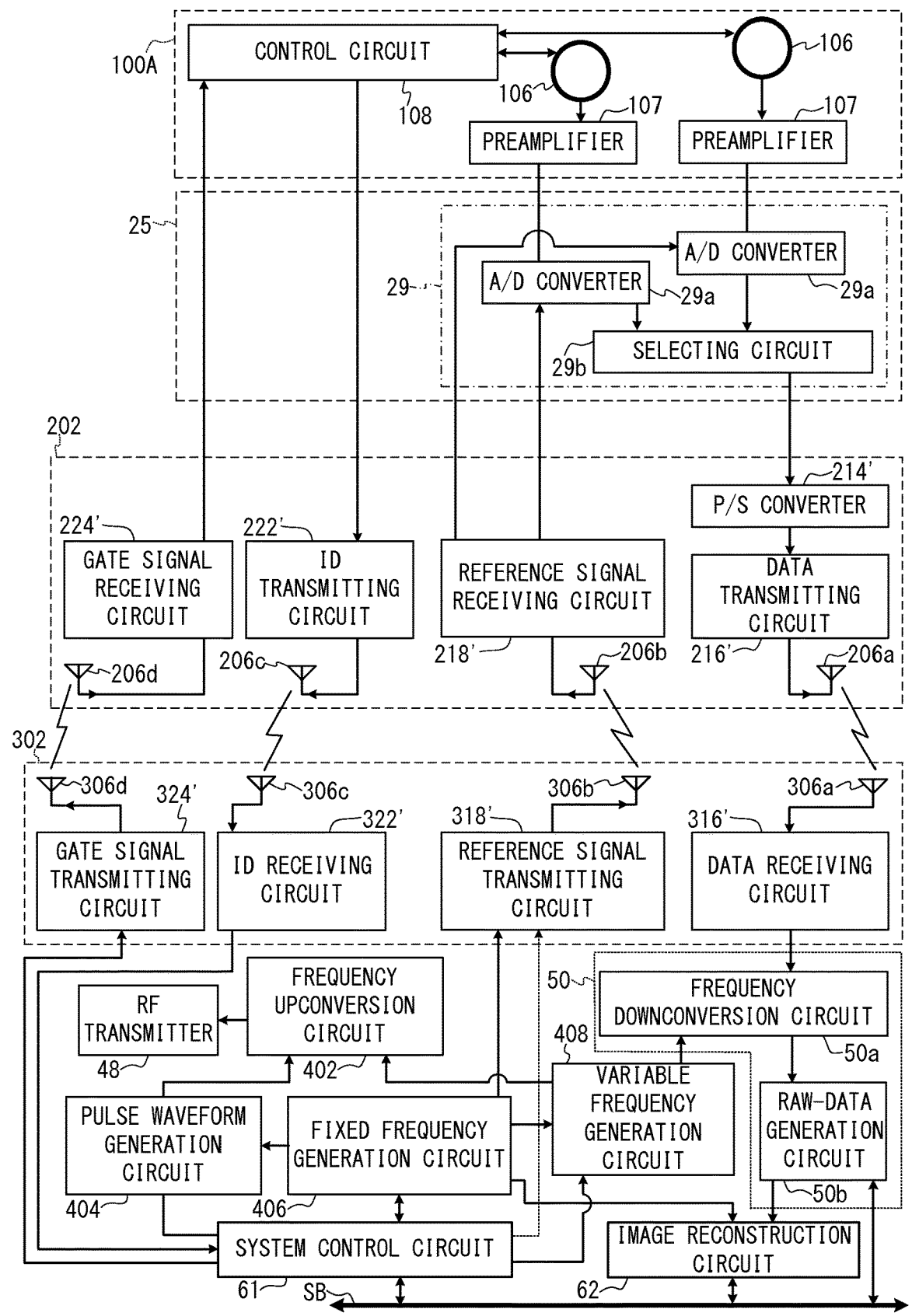
FIG. 19 is a block diagram showing an example of the configuration relevant to the digital radio communication system of MR signals, in the MRI apparatus of the third embodiment.

FIG. 19 is a block diagram showing an example of the configuration relevant to the digital radio communication system of the MR signals, in the MRI apparatus 10E of the third embodiment. Only two components of the coil elements 106 and only two components of the preamplifiers 107 of the RF coil device 100A are shown in FIG. 19 for the same reason as FIG. 6. The configuration of the connection ports 25 of the table 22 is the same as the first embodiment.

As shown in FIG. 19, inside the chassis 202 of the connector 27e of the bed 20, a P/S converter 214', a data transmitting circuit 216', a reference signal receiving circuit 218', an ID transmitting circuit 222', and a gate signal receiving circuit 224' are disposed in addition to the antennas 206a to 206d.

Inside the chassis 302 of the connector 37e of the gantry 30, a data receiving circuit 316', a reference signal transmitting circuit 318', an ID receiving circuit 322', and a gate signal transmitting circuit 324' are disposed in addition to the antennas 306a to 306d.

Next, the four radio communication pathways will be explained. Although the radio communication via an induced electric field is performed at least in the pathway between the antennas 206a and 306a, it may be performed in the pathway between the antennas 206b and 306, and/or the pathway between the antennas 206d and 306d.

Firstly, in the pathway between the antennas 206c and 306c, the identification information of the RF coil device 100A is transmitted. More specifically, for example, if the antenna 306c of the ID receiving circuit 322' gets close to the antenna 206c of the ID transmitting circuit 222', the ID transmitting circuit 222' operates based on electric power wirelessly supplied from the ID receiving circuit 322'.

In other words, the ID transmitting circuit 222' acquires the identification information of the RF coil devices 100A by wire from the control circuit 108 of the RF coil device 100A, via the cable 102, the connector 101 (FIG. 3), and one of the connection ports 25. The ID transmitting circuit 222' automatically wirelessly transmits the acquired identification information from the antenna 206c to the antenna 306c as a digital signal. This radio communication of the identification information may be performed in the same way as RFID (Radio Frequency Identification) typified by, for example, IC (Integrated Circuit) tag.

The ID receiving circuit 322' outputs the identification information of the RF coil device 100A received by the antenna 306c to the system control circuit 61.

Secondly, in the pathway between the antennas 306d and 206d, a gate signal similar to the above-mentioned gate signal is continuously wirelessly transmitted from the gate signal transmitting circuit 324' of the gantry 30 side to the gate signal receiving circuit 224' of the bed 20 side during imaging.

Thirdly, in the pathway between the antennas 306b and 206b, the trigger signal and the reference signal are continuously wirelessly transmitted from the reference signal transmitting circuit 318' of the gantry 30 side to the reference signal receiving circuit 218' of the bed 20 side during imaging, in the way similar to the above-mentioned manner. The trigger signal and the reference signal are inputted to each of the A/D converters 29a of the digital processing circuit 29 of each of the connection ports 25.

Fourthly, in the pathway between the antennas 206a and 306a, the digitized MR signals are wirelessly transmitted from the data transmitting circuit 216' of the bed 20 side to the data receiving circuit 316' of the gantry 30 side, via an induced electric field.

More specifically, the MR signals (digitized by the direct sampling method) from the coil elements 106 selected for imaging are transmitted from the selecting circuit 29b to the P/S converter 214' in the way similar to the first embodiment. If at least two of the coil elements 106 are selected for detection, the P/S converter 214' converts the plural MR signals from parallel signals into a serial signal for wireless transmission, and outputs the serial signal to the data transmitting circuit 216'.

However, the present embodiment is not limited to an aspect of transmitting the MR signals as a serial signal. For example, the MR signals may be wirelessly transmitted as parallel signals by increasing the number of antennas for transmitting and receiving MR signals.

The data transmitting circuit 216' generates a serial and digital signal for radio transmission (in which original plural MR signals are included) by performing various types of processing such as error correction encoding, interleave, modulation, frequency conversion, amplification, and filtering on the inputted serial MR signal.

Note that, since the short-distance radio transmission via an induced electric field is performed here, the radio output intensity of the above MR signal does not need to be raised to as strong level as the radio output level of the remote radio communication. The antenna 206a wirelessly transmits the MR signals for radio transmission inputted from the data transmitting circuit 216' to the antenna 306a.

The data receiving circuit 316' performs various types of processing such as amplification, frequency conversion, demodulation, deinterleave, and error correction decoding on the serial MR signal received by the antenna 306a. Thereby, the data receiving circuit 316' extracts the original digitized MR signals from the serial MR signal for radio transmission, and outputs the extracted MR signals to the frequency downconversion circuit 50a of the RF receiver 50. After this, the MR signals are subjected to the same processing as the first embodiment.

Note that, as to the gate signal, it may be superimposed on the reference signal in the way similar to the trigger signal. In this case, since the number of radio communication pathways can be decreased by one by omitting components such as the antennas 206d and 306d, configuration can be streamlined.

Figure 20:
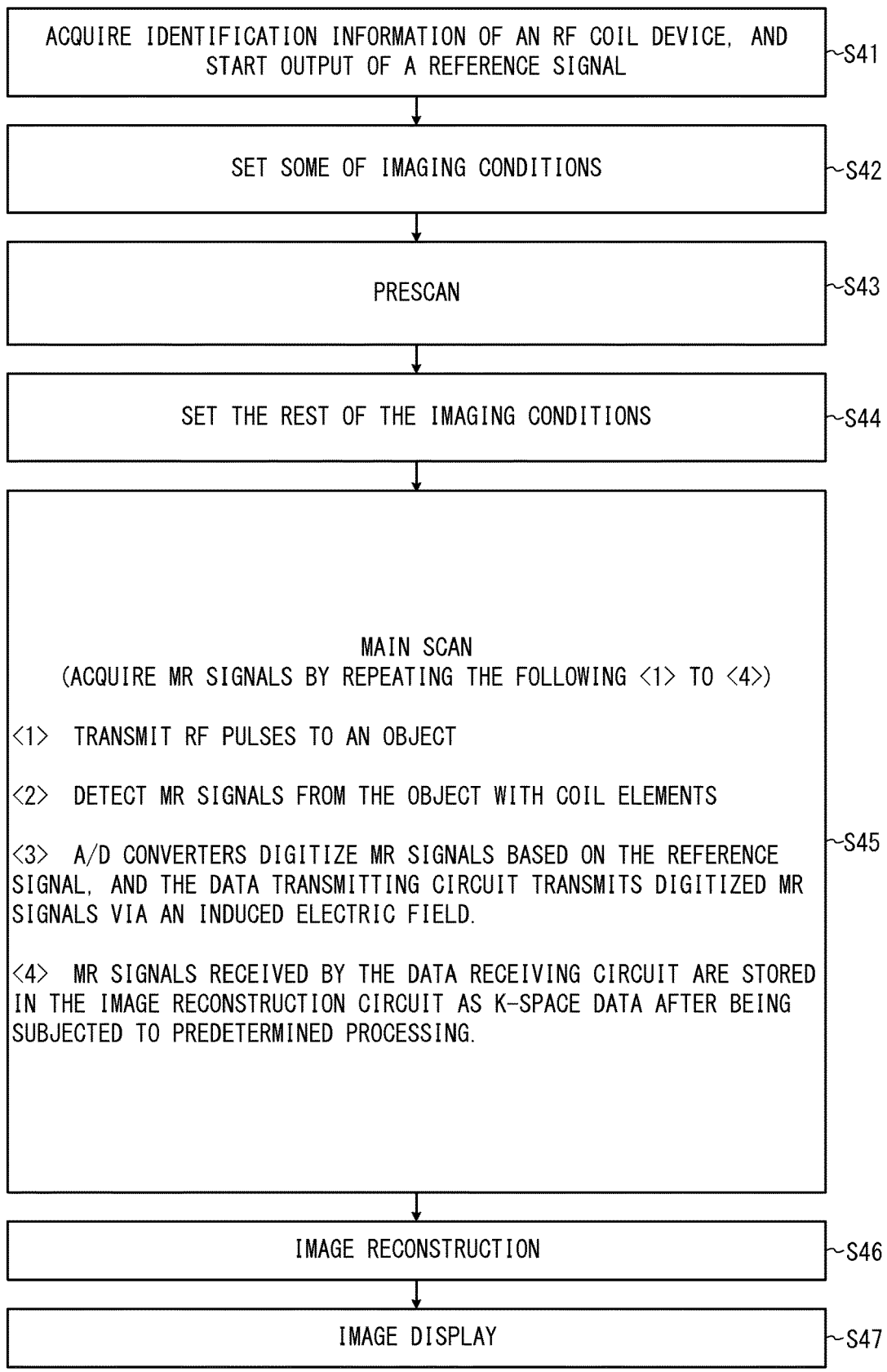
FIG. 20 is a flowchart illustrating an example of a flow of an imaging operation performed by the MRI apparatus of the third embodiment.

FIG. 20 is a flowchart illustrating an example of a flow of an imaging operation performed by the MRI apparatus 10E of the third embodiment. In the following, according to the step numbers in the flowchart shown in FIG. 20, an operation of the MRI apparatus 10E will be described by referring to the above-mentioned FIG. 17. to FIG. 19 as required.

[Step S41] The connector 27e of the bed 20 and the connector 37e of the gantry 30 are coupled and fixed to each other (see FIG. 18). Then, the RF coil device 100A is similarly attached on the object P, and the RF coil device 100A is connected to one of the connection ports 25 (see FIG. 17). Thereby, as explained with FIG. 19, the identification information of the RF coil device 100A is automatically wirelessly transmitted from the ID transmitting circuit 222' to the ID receiving circuit 322' in the pathway between the antennas 206c and 306c, and this identification information is transmitted to the system control circuit 61.

Thereby, the system control circuit 61 recognizes that the RF coil device 100A is currently connected, outputs the permission of further communication between the RF coil device 100A and the control device 40, and causes each component of the MRI apparatus 10E to supply electric power to the RF coil device 100A via one of the connection ports 25 and so on, in the above-mentioned manner.

In addition, the reference signal transmitting circuit 318' generates the reference signal in the way similar to the reference signal generation circuit 414 of the first embodiment. The reference signal transmitting circuit 318' starts outputting the reference signal in accordance with the communication permission outputted by the system control circuit 61 (the reference signal is continuously wirelessly transmitted). Note that the trigger signal is superimposed on the reference signal to be transmitted.

In addition, the table moving structure 23 moves the table 22 into inside of the gantry 30 in accordance with the control signal from the system control circuit 61 inputted via each of the connectors 37e and 27e.

Afterward, the processing proceeds to the Step S42.

[Step S42 to S44] The processing of each of the Steps S42 to S44 is the same as the processing of each of the Steps S2 to S4 of the first embodiment.

Afterward, the processing proceeds to the Step S45.

[Step S45] The system control circuit 61 causes the MRI apparatus 10E to perform the main scan by controlling each component thereof.

More specifically, the static magnetic field formed in the imaging space is uniformed by the shim coil 32 in the above-mentioned manner.

During the implementation term of the main scan, the gate signal transmitting circuit 324' generates the gate signal in the way similar to the gate signal generation circuit 418 of the first embodiment, and continuously wirelessly transmits the gate signal to the gate signal receiving circuit 224'. This gate signal is continuously transmitted from the gate signal receiving circuit 224' to the control circuit 108 of the RF coil device 100A.

After this, when the system control circuit 61 receives a command of start of imaging from the input device 72, the MR signals from the object P are acquired by repeating the processing composed of the following sub-steps <1> to <4> in series, for example.

<1> The gradient magnetic fields are formed and the RF pulses are transmitted to the object P, in the same way as mentioned above. Only during the transmission period of the RF pulses, the gate signal is set to, for example, on-level.

<2> The gate signals is switched over to, for example, off-level after transmission of the RF pulses, and the MR signals from the object P are detected by each of the coil elements 106, then amplified by the preamplifiers 107 and then inputted to each of the A/D converters 29*a* (FIG. 19), in the same way as mentioned above.

<3> Each of the A/D converters 29*a* starts sampling and quantization of the MR signals based on the reference signal in synchronization with the timing when the trigger signal is wirelessly transmitted, and outputs the digitized MR signals to the selecting circuit 29*b*.

The selecting circuit 29*b* transmits the digitized MR signals from the coil elements 106 selected for imaging to the P/S converter 214' of the radio communication device 28.

The P/S converter 214' converts the inputted plural MR signals into a serial signal, and outputs the serial signal to the data transmitting circuit 216'.

The data transmitting circuit 216' generates the serial and digital signal for radio transmission (in which plural original MR signals are included) by performing the predetermined processing on the serial MR signal as explained in FIG. 19, and wirelessly transmits the generated serial and digital signal for radio transmission from the antenna 206*a* to the antenna 306*a* via an induced electric field.

<4> The data receiving circuit 316' extracts the original digital MR signals by performing the predetermined processing on the serial signal for radio transmission received by the antenna 306*a*. The data receiving circuit 316' outputs the extracted MR signals to the frequency downconversion circuit 50*a*. After this, the raw data of the MR signals are converted into k-space data and then stored in the image reconstruction circuit 62, in the way similar to the first embodiment.

After completion of acquisition of the MR signals by repeating the processing of the above sub-steps <1> to <4>, the processing proceeds to the Step S46. Incidentally, the analogue MR signals outputted from the reception RF coil 24 inside the table 22 are digitized under the direct sampling method by another digital processing circuit (not shown) inside the table 22, then inputted to the chassis 202 and then acquired in the way similar to the above-mentioned method.

[Step S46, S47] The processing of the Steps S46 and S47 is the same as the processing of the Steps S6 and S7 in the first embodiment. The foregoing is a description of the operation of the MRI apparatus 10E according to the third embodiment.

As described above, the same effects as the first embodiment are obtained in the third embodiment. Moreover, in the third embodiment, the transmission side and the receiving side are closely fixed to each other at the time of radio communication, and the radio communication of the MR signals via an induced electric field is performed. Therefore, since output power of the radio communication can be more lowered than digital radio communication of conventional technology, the MRI apparatus 10E of the present embodiment easily accommodates to legal regulations in various countries.

In addition to the closely-situated transmission side and receiving side, output power of the radio communication can be lowered. Therefore, the problem that the transmitted radio waves are reflected off surrounding areas and this degrades own data of radio communication does not occur. Thus, digitized MR signals can be wirelessly transmitted satisfactorily from the RF coil device 100A to the control device 40 of the MRI apparatus 10E.

Furthermore, the MR signals detected by the coil elements 106 are converted into a serial signal and then wirelessly transmitted. Thus, the necessary number of an antenna for transmitting the MR signals (radio communication pathway) is only one pair, and frequency separation for preventing interference is not necessary between each of the MR signals.

By contrast, in the radio communication of digital MR signals in conventional technology, the receiving side is located far away from the transmission side. Thus, in the (remote) radio communication of digital MR signals in the conventional technology, frequency separation and time-multiplexed communication are performed, because interference such as cross talk occurs if plural coil elements for detecting MR signals are simultaneously connected. In short-distance radio communication like the third embodiment, it is not necessary to perform time-multiplexed communication.

In addition, because (a) the electric power supply to the RF coil devices 100A, (b) the transmission of the gate signal and (c) the transmission of the trigger signal are wirelessly performed, configuration of the MRI apparatus 10E can be simplified. As a result, cost of manufacturing the MRI apparatus 10E can be reduced.

As to the third embodiment, the following two supplementary notes are added.

Firstly, though an example in which the gate signal and the reference signal are wirelessly transmitted via an induced electric field has been described, embodiments of the present disclosure are not limited to such an aspect. For example, as one of other configurations, the gate signal and the reference signal may be transmitted by wire and only the MR signals may be wirelessly transmitted via an induced electric field.

Secondly, as an example in the third embodiment, (a) the chassis 202 and 302 functioning as radio communication devices are respectively disposed to the entrance side of the gantry 30 and the gantry 30 side of the bed 20 and (b) the chassis 202 and 302 are electromagnetically connected to each other by interdigitating the connectors 27*e* and 37*e* each other. However, this is only an example of arrangements of radio communication devices (the chassis 202 and 302).

For instance, the chassis 202 may be disposed on the end of the cable exposed out of the table 22, the MR signals via one of the connection ports 25 may be transmitted to the chassis 202 at the end of the cable, and connection structure that detachably fixes the chassis 202 may be disposed on the exterior wall of the gantry 30. Then, the chassis 302 may be buried to such a position that the chassis 302 is electromagnetically connected with the chassis 202 when the chassis 202 is fixed to the exterior wall of the gantry 30.

<Supplementary Notes of Each Embodiment>

[1] In each of the above embodiments, since the MR signals are digitized by the direct sampling method in an early stage such as, for example, inside of the RF coil device 100B or inside of the connection ports 25 of the table 22, contamination of noise into the MR signals is suppressed with a simple device configuration.

In this case, manufacturing cost may increase due to redesign of the table 22 and the entirety of the bed 20. For this reason, an MRI apparatus may be configured so that a conventional bed is used and the above-mentioned effect is obtained depending on conditions.

Accordingly, as a modification of each of the above embodiments, an MRI apparatus 10F may be configured to include a conventional bed without the digital processing circuit 29 in the table 22 and to have the above effects only in the case of using a wireless type RF coil device. In this case, though the above effects are not obtained in the case of using a cable type RF coil device such as the RF coil device 100A, it has a merit of reducing manufacturing cost by using the conventional bed.

Figure 21:
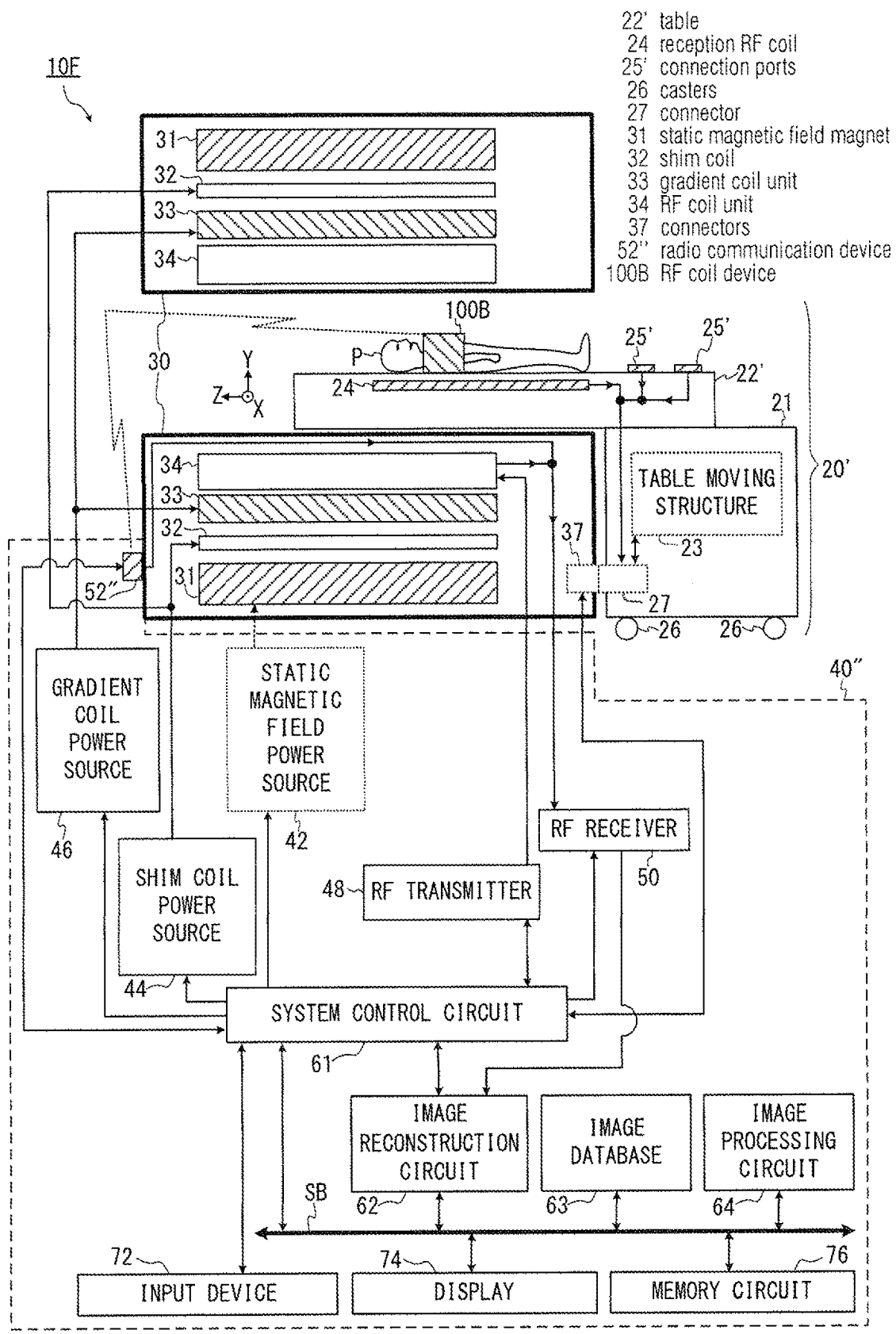
FIG. 21 is a block diagram showing an example of overall configuration of a modification of the MRI apparatus of each embodiment.

FIG. 21 is a block diagram showing an example of overall configuration of the modification of the MRI apparatus 10F of each embodiment. In FIG. 21, the bed 20' of the MRI apparatus 10F is the same as a conventional bed, and does not include the radio communication device 28 of the first embodiment. In addition, each of the connection ports 25' of its table 22' of the MRI apparatus 10F does not include the digital processing circuit 29 (similar to FIG. 11).

In FIG. 21, the RF coil device 100B digitizes MR signals by the direct sampling method, and wirelessly transmits the digitized MR signals (see the second embodiment). The control device 40" of the MRI apparatus 10F includes a radio communication device 52" fixed on the exterior wall of the gantry 30. The radio communication device 52" receives electromagnetic waves of the digitized MR signals wirelessly transmitted from the RF coil device 100B, then extracts original MR signals from the electromagnetic waves, and then outputs the extracted MR signals to the RF receiver 50.

By contrast, when the RF coil device 100A of cable type is used, its connector 101 is connected to the connection port 25' and operates in the same way as a conventional MRI apparatus (in this case, the radio communication device 52" does not operate).

[2] Correspondences between terms used in the claims and terms used in the embodiments explained above will be described. Note that the correspondences described below are just some of possible interpretations for reference and should not be construed as limiting embodiments of the present invention.

The RF coil device 100A to be attached on the object P and the reception RF coil 24 are examples of the RF coil described in the claims.

In the first embodiment, the antenna 28c is an example of the first antenna described in the claims and the antenna 52b is an example of the second antenna described in the claims (see FIG. 6).

In the first embodiment, all the components of the radio communication device 28 excluding the antenna 28c are an example of the first radio communication circuitry described in the claims.

In the first embodiment, all the components of the radio communication device 52 excluding the antenna 52b are an example of the second radio communication circuitry described in the claims.

In the second embodiment, the antennas 230a to 230d (FIG. 14) and the antenna 28c (FIG. 15) are examples of the first antenna described in the claims.

In the second embodiment, the antennas 330a to 330d are an example of the second antenna described in the claims (see FIG. 14 and FIG. 15).

In the second embodiment, the data transmitting circuit 216 (FIG. 14) is an example of the first radio communication circuitry described in the claims, and all the components of the radio communication device 28 excluding the antenna 28c (FIG. 15) are also an example of the first radio communication circuitry described in the claims.

In the second embodiment, all the components of the radio communication device 52' excluding the antennas 330a to 330d are an example of the second radio communication circuitry described in the claims.

In the third embodiment, the antennas 206a to 206d are an example of the first antenna described in the claims and the antennas 306a to 306d are an example of the second antenna described in the claims (see FIG. 19).

In the third embodiment, all the components of the chassis 202 excluding the antennas 206a to 206d are an example of the first radio communication circuitry described in the claims.

In the third embodiment, all the components of the chassis 302 excluding the antennas 306a to 306d are an example of the second radio communication circuitry described in the claims.

The connector 27e of the bed 20 is an example of the first connector described in the claim.

The connector 37e of the gantry 30 is an example of the second connector described in the claim.

The RF coil device 100B is an example of the wireless type RF coil described in the claims.

In the second modification of the first embodiment (FIG. 11), all the components of the relay unit 160 excluding the chassis 162 are an example of the relay circuit described in the claims.

[3] While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
   a bed on which an object is loaded;
   a wired RF coil configured to receive first nuclear magnetic resonance (NMR) signals from the object and output the first NMR signals as analogue signals;
   a digital processing circuit configured to be disposed inside the bed and digitize the first NMR signals;
   first radio communication circuitry configured to wirelessly transmit the first NMR signals digitized by the digital processing circuit;
   a wireless RF coil configured to receive and digitize second NMR signals and to wirelessly transmit the digitized second NMR signals;
   second radio communication circuitry configured to receive the first or second digitized and wirelessly transmitted NMR signals; and
   an image reconstruction circuit configured to reconstruct image data based on the first or second digitized NMR signals received by the second radio communication circuitry,
wherein the second radio communication circuitry also receives identification information indicating whether a wired RF coil or a wireless RF coil is connected for use and (a) when the identification information indicates a wired RF coil is connected, the second radio communication circuitry wirelessly receives the first NMR signals and (b) when the identification information indicates a wireless RF coil is connected, the second radio communication circuitry wirelessly receives the second NMR signals.

2. The magnetic resonance imaging apparatus according to claim 1, wherein the digital processing circuit is configured to digitize the first NMR signals using a direct sampling method.

3. The magnetic resonance imaging apparatus according to claim 1, wherein:
the bed includes a table on which the object is loaded and a supporting platform which movably supports the table; and
the first radio communication circuitry is disposed inside the supporting platform.

4. The magnetic resonance imaging apparatus according to claim 3, further comprising:
a gantry configured to be installed in an imaging room and to apply a static magnetic field to an imaging space in which the object is set during imaging, and
wherein the second radio communication circuitry is disposed on a wall of the imaging room.

5. The magnetic resonance imaging apparatus according to claim 1, further comprising:
a gantry configured to apply a static magnetic field to an imaging space in which the object is set;
a first connector configured to be disposed in the bed and include the first radio communication circuitry that is configured to wirelessly transmit the digitized first NMR signals via an induced electric field; and
a second connector configured to be disposed in the gantry and include the second radio communication circuitry that is configured to receive the digitized first NMR signals wirelessly transmitted by the induced electric field,
wherein when the first and second connectors are coupled with and fixed to each other the digitized first NMR signals are wirelessly transmitted from the first radio communication circuitry to the second radio communication circuitry using the short-distance radio communication via the induced electric field.

6. The magnetic resonance imaging apparatus according to claim 1, further comprising:
a relay circuit configured to be connected in series between the wired RF coil and the bed,
wherein
the bed includes a connection port connectable to the relay circuit;
the relay circuit includes
(a) an input side connector connected to the wired RF coil by wire,
(b) an A/D converter configured to digitize the analogue first NMR signals acquired from the wired RF coil via the input side connector using a direct sampling method, and
(c) an output side connector configured to be connected to the connection port of the bed and to output the NMR signals digitized by the A/D converter.

7. A magnetic resonance imaging (MRI) apparatus comprising:
a bed on which an object is loaded;
a gantry configured to apply a static magnetic field to an imaging space in which the object is set;
a wired RF coil configured to receive nuclear magnetic resonance (NMR) signals emitted from the object and output the NMR signals as analogue signals;
a digital processing circuit configured to be disposed inside the bed and digitize the NMR signals;
a first connector configured to be disposed in the bed, and include first radio communication circuitry that is configured to wirelessly transmit the digitized NMR signals using a short-distance radio communication via an induced electric field; and
a second connector configured to be disposed in the gantry and include second radio communication circuitry that is configured to wirelessly receive the digitized NMR signals using the short-distance radio communication via the induced electric field;
wherein, when the first and second connector are coupled with and fixed to each other, the NMR signals are wirelessly transmitted from the first radio communication circuitry to the second radio communication circuitry using the short-distance radio communication via the induced electric field.

* * * * *